United States Patent
Vidal-De-Miguel

(10) Patent No.: US 8,378,297 B2
(45) Date of Patent: Feb. 19, 2013

(54) METHOD AND APPARATUS TO PRODUCE STEADY BEAMS OF MOBILITY SELECTED IONS VIA TIME-DEPENDENT ELECTRIC FIELDS

(76) Inventor: Guillermo Vidal-De-Miguel, Madrid (ES)

( * ) Notice: Subject to any disclaimer, the term of this patent is extended or adjusted under 35 U.S.C. 154(b) by 235 days.

(21) Appl. No.: 12/748,623

(22) Filed: Mar. 29, 2010

(65) Prior Publication Data
US 2010/0243883 A1   Sep. 30, 2010

Related U.S. Application Data

(60) Provisional application No. 61/211,111, filed on Mar. 30, 2009.

(51) Int. Cl.
*H01J 49/04* (2006.01)
*H01J 49/26* (2006.01)
*H01J 49/42* (2006.01)

(52) U.S. Cl. ......... 250/290; 250/282; 250/288; 250/281

(58) Field of Classification Search .................. 250/281, 250/282, 290, 292, 293, 288
See application file for complete search history.

(56) References Cited

U.S. PATENT DOCUMENTS

| | | | | |
|---|---|---|---|---|
| 7,170,053 B2 * | 1/2007 | Shvartsburg et al. | ......... | 250/287 |
| 7,547,879 B2 * | 6/2009 | Miller et al. | .................. | 250/286 |
| 7,829,849 B2 * | 11/2010 | Giles | ............................. | 250/290 |
| 7,863,562 B2 * | 1/2011 | Wollnik et al. | ............... | 250/292 |
| 7,868,289 B2 * | 1/2011 | Cousins et al. | ............... | 250/292 |
| 2005/0263699 A1 * | 12/2005 | Miller et al. | .................. | 250/292 |
| 2007/0200059 A1 * | 8/2007 | Tang et al. | .................... | 250/288 |
| 2007/0272852 A1 * | 11/2007 | Miller et al. | .................. | 250/288 |
| 2008/0164409 A1 * | 7/2008 | Schultz et al. | ............... | 250/282 |
| 2008/0210861 A1 * | 9/2008 | Wu et al. | ....................... | 250/287 |
| 2009/0189064 A1 * | 7/2009 | Miller et al. | .................. | 250/282 |
| 2009/0189070 A1 * | 7/2009 | Clemmer et al. | ............. | 250/282 |
| 2009/0309015 A1 * | 12/2009 | Schultz et al. | ............... | 250/281 |
| 2010/0207022 A1 * | 8/2010 | Tang et al. | .................... | 250/282 |
| 2011/0049356 A1 * | 3/2011 | Fernandez De La Mora | .......................... | 250/283 |
| 2011/0139972 A1 * | 6/2011 | Hardman et al. | .......... | 250/252.1 |

* cited by examiner

*Primary Examiner* — David A Vanore
*Assistant Examiner* — Wyatt Stoffa
(74) *Attorney, Agent, or Firm* — Hoffmann & Baron, LLP

(57) ABSTRACT

A method to select ions based on their electrical mobility is described. Ions are separated in space, and a continuous flow of mobility filtered ions is produced at the outlet of the device, as in Differential Mobility Analyzers (DMAs). Yet, no high fluid velocity field is required, avoiding limitations associated in DMAs to flow unsteadiness. Instead, separation relies on the use of time-dependent electric fields. Separation is based on synchronizing the period of the field with the flight time of an ion from an inlet to an outlet for a particular electrical mobility.
Unlike FAIMS, the new invention separates ions according to their absolute mobility within one or a few characteristic times for field variation, rather than via many tiny separation steps over many periods of field variation producing separation according to non-linearities in the mobility. Unlike conventional pulsating ion mobility spectrometry, a steady flow of ions is produced.

20 Claims, 17 Drawing Sheets

METHOD AND APPARATUS TO PRODUCE STEADY BEAMS OF MOBILITY SELECTED IONS VIA TIME-DEPENDENT ELECTRIC FIELDS

CROSS REFERENCE TO RELATED APPLICATION

This application claims the benefit of priority U.S. Provisional Patent Application No. 61/211,111 filed on Mar. 30, 2009, the entire contents of which are incorporated herein.

U.S. PATENTS AND APPLICATIONS CITED

Labowsky; Michael J., Fenn; John B., Yamashita; Masamichi (1985) Method and apparatus for the mass spectrometric analysis of solutions, U.S. Pat. No. 4,531,056, Jul. 23, 1985

U.S. Pat. No. 6,107,628; Keqi Tang, Mikhail B. Belov, Aleksey V. Tolmachev, Harold R. Udseth, Richard D. Smith; Multi-source ion funnel; Mar. 25, 2003.

Flagan, Richard C. and Zhang, Shou-Hua (1997), Radial differential mobility analyzer. U.S. Pat. Nos. 5,596,136 (Jan. 21, 1997) and 5,606,112 (Feb. 25, 1997).

Fernández de la Mora, J., L., de Juan, T. Eichler and J. Rosell (1999), Method and apparatus for separating ions in a gas for mass spectrometry; U.S. Pat. Nos. 5,869,831 (9 Feb. 1999) and 5,936,242 (10 Aug. 1999)

U.S. Pat. No. 5,420,424 Ion Mobility Spectrometer; Byron L. Carnahan, Alexander S. Tarassov, May 30, 1995.

Guevremont; Roger, Purves; Randy, Parallel plate geometry FAIMS apparatus and method, U.S. Pat. No. 6,806,466

OTHER PATENTS AND APPLICATIONS CITED

Labowsky, Michael J. and Juan Fernández de la Mora, Ion mobility separation devices, International Application published under the patent cooperation treaty (PCT); PCT publication WO2004/077016; PCT/US2004/005133; Sep. 10, 2004

U.S. patent application Ser. No. 11/786/688; J. Rus, J. Fernandez de la Mora, Resolution improvement in the coupling of planar differential mobility analyzers with mass spectrometers or other analyzers and detectors. 11 Apr. 2007. Publication 20080251714, October 2008; PCT/EP2008/053762, publication WO2008/125463

U.S. patent application Ser. No. 12/070,937, J. Fernández de la Mora, A. Casado, G. Fernández de la Mora, Method to accurately discriminate gas phase ions with several filtering devices in tandem, 24 Feb. 2007; publication 20080203290, 28 Aug. 2008.

U.S. patent application Ser. No. 11/732,770; Martinez-Lozano P., Fernandez de la Mora J.; Method for detecting volatile species of high molecular weight; Apr. 4, 2006.

U.S. provisional patent application 61/204,996; Improved ionizer for vapor analysis decoupling the ionization region from the analyzer; Guillermo Vidal-de-Miguel G. 14 Jan. 2009

Fernández de la Mora, J. and J. Rus, The use of Multipole ion guides with rods of small dimensions to concentrate small charged species in a gas at relatively high pressure, U.S. provisional patent application US60/857,231 (Dec. 7, 2006).

OTHER DOCUMENTS CITED

[1] Fenn J B, Mann M, Meng C K, Wong S F, Whitehouse C M, Electrospray ionization for mass-spectrometry of large biomolecules. Science 246 (4926): 64-71, 1989

[2] Whitehouse, C. M., Levin, F., Meng, C. K. and Fenn, J. B., Proc. 34th ASMS Conf. on Mass Spectrom. and Allied Topics, Denver, 1986, p. 507.

[3] High-Resolution Ion Cyclotron Mobility Spectrometry, Samuel I. Merenbloom, Rebecca S. Glaskin, Zachary B. Henson, and David E. Clemmer; Department of Chemistry, Indiana University, Bloomington, Ind. 47405; 14 Jan. 2009

[4] Labowsky M., and J. Fernandez de la Mora, Novel ion mobility analyzers and filters, J. Aerosol Science, 37(3) 340-362, 2006.

FIELD OF THE INVENTION

The present invention relates to an apparatus and a method to select ions based on their electrical mobility. Ions are separated in space according to their electrical mobility Z, and a continuous flow of selected ions with a narrow range of mobility is delivered to the outlet of the device, as in Differential Mobility Analyzers (DMAs). Yet, no high fluid velocity field is required, avoiding limitations associated in DMAs to flow unsteadiness, compressibility and turbulent transition. Instead, separation relies on the use of curved time-dependent ion trajectories produced by time-dependent electric fields. Another advantage of the new invention when compared with DMAs is that no pump is required, and limitations associated to the operation of the pump, i.e. temperature of the gas, are also avoided. Unlike FAIMS, full separation takes place within one or a few characteristic times for field variation, and separation is based on the direct measurement of the mobility, rather than on many tiny contributions accumulated over many periods of field variation of the non-linear dependence of the mobility on the electric field. In one preferred embodiment, separation is based on synchronizing the period of the field with the flight time of an ion from an inlet to an outlet for a particular electrical mobility. Unlike conventional pulsating ion mobility spectrometry, a nearly steady flow of mobility-selected ions is obtained.

BACKGROUND OF THE INVENTION

Selection and analysis of ions and charged aerosols by means of their physical properties is very useful for many applications including chemical analysis, environmental analysis, for the production of small particles of controlled size, for nano-technological applications and related scientific studies, etc. The present invention can be used with charged particles suspended in a gas, where the term charged particles should by understood in its broadest sense as particles of any size whose net electrical charge is different from zero. However, for simplicity, charged particles and ions will all be referred to as ions.

Any apparatus used to select, analyze or measure is characterized by its sensitivity and its resolution. Analyzers are used to measure key properties of the substances under study. The sensitivity refers to the minimum amount of substance that the apparatus is able to sense or work with, while the resolution refers to the smallest difference in such key properties that the apparatus can distinguish. A widely used definition of the Resolution is based on the Full With at Half Maximum algorithm (FWHM). Applying this definition to a Gaussian peak yields $$R_{gauss} = \frac{\mu}{\sigma \cdot 2 \cdot \sqrt{2 \cdot \ln 2}}$$

where μ and σ are, respectively, the mean and the standard deviation.

Among the most commonly used ion analyzers, Mass Spectrometers, also termed MS, produce information very relevant to the chemical structure and composition of ions with very high resolution and very high sensitivity. There are different types of mass spectrometers, but they all have in common that the ions are separated according to mass/charge due to the mass/charge dependence of their motion when subjected to specific electric and magnetic fields in vacuum. The present invention can be coupled to an MS trough a simplified version of an API system. The API interface (Atmospheric Pressure Interface) requires some more detail that will later provide a background for the present invention. The MS inlet is most often a small orifice in a plate or the bore of a capillary, through which gas and ions are sampled at sonic speed into the vacuum system of the MS. To prevent neutral vapors from entering the MS, a counterflow dry gas is sometimes interposed between the electrospray and the atmospheric inlet of the MS. Ions are pushed forward by the electric field while neutral species and droplets are dragged away by the counterflow. See Refs [1] [2], and U.S. Pat. No. 4,531,056.

Complex samples produce very complex spectra difficult to evaluate. Big proteins are also difficult to analyze by simple MS techniques. Either because the high amount of different compounds produce overlapped peaks in the mass spectrum or because there are many isomers and many charged states for each mass, the spectrum produced by simple MS when the amount of different substances is very complicated tends to be difficult to interpret if not impossible. Tandem analysis techniques are a very powerful tool which allows unfolding a complex spectrum over more than one variable.

Ions can also be separated according to their electric drift velocity in a bath gas. More specifically, ions can be selected or characterized by their electrical Mobility Z, defined as the ratio of electric velocity to electric field. Note that, at atmospheric pressure, the effect of magnetic force is usually negligible because ionic speed is limited and the effect of electric fields is substantially stronger than the effect of state of the art magnetic fields. Using the definition of mobility, the electric velocity of an ion is:

$$\vec{V}_E = Z \cdot \vec{E} \quad (1)$$

where $V_E$ stands for the electric velocity of the ions induced by the electric field, and E stands for the electric field. And the total velocity of the ion is the sum of the electric velocity plus the fluid velocity:

$$\frac{d\vec{X}}{dt} = \vec{V}_E + \vec{V}_f = Z \cdot \vec{E} + \vec{V}_f \quad (2)$$

where $V_f$ stands for the fluid velocity, X stands for the position of the ion, and t is the time.

The mass of an ion is a very specific and useful information, since it is directly related to its composition. The mobility is not related to the structure of the ion so directly, but it still gives some information on its structure. Basic kinetic theory states that mobility is inversely proportional to the collision cross section and the square root of the reduced mass of the ion and the gas molecules. Heavier molecules usually have lower mobility. Isomers having identical masses can still be differentiated according to their mobility when they have different cross sections. Various methods have been used to separate ions according to their electrical mobility.

IMS: Ion Mobility Spectrometry consist of a pulsed gate, which produces packets of ions, followed by a drift tube, in which an axial steady electric field parallel to the drift tube pushes the ions along the axis of the drift tube towards a detector at the end of the drift tube. The gas is usually at rest and the fluid velocity is usually negligible compared to the electric velocity. When the gate produces a packet of ions at time $t=t_0$, the different ions enter simultaneously in the drift tube. Once in the drift tube, each different type of ion drifts at a different electric velocity. Therefore, the original packet of ions is separated into different packet of ions according to their mobility. Ions reach the sensor at time $$t = t_0 + \frac{l}{Z \cdot E}.$$

More mobile ions travel faster and reach the sensor before less mobile ions which travel slower. After each pulse of the gate, the IMS produces a full spectrum of the sample. As ions travel along the drift tube, the different packets of ions of the same mobility are also broadened by Brownian diffusion which limits the resolution achievable by IMS techniques. The resolution achieved in a drift tube depends on the length of the drift tube, but typical resolutions can be around 100. Resolution in an IMS spectrum is defined as $R_{IMS}=\tau/\delta\tau$, where 'τ' is the time required to travel along the drift tube and 'dτ' is the duration of the signal produced by the packet of ions. The time τ is equal to $\tau=l/V_E$, where l is the length of the drift tube, while $\delta\tau=\sigma/V_E$ where σ is the size of the broadened packet of ions. On the other hand, σ is given by: $\sigma=\sqrt{2 \cdot D \cdot \tau}$, where D is the diffusion coefficient of the ion in the gas. Finally, using Einstein equation, which states that $$D = Z \cdot \frac{k_B \cdot T}{e},$$

where $k_B$ is the Boltzmann constant and T is the temperature of the gas, and e is the charge of the ion, a first approximation to the IMS resolution is:

$$R_{IMS} = \sqrt{\frac{l \cdot E \cdot e}{2 \cdot k_B \cdot T}} \quad (3)$$

Numerous methods have been used to increase the resolution and the duty cycle of IMS instruments. Of particular relevance to the present invention have been various attempts to do so by synchronization of various gates or various electric fields applied in various regions separated by gates or electrodes subject to sequences of voltages:

Resolution can be increased by increasing the applied high voltage l·E But, too high voltages can be difficult to produce, they are difficult to handle and, in any case, too high voltages can be dangerous. A solution to this problem is using a sequence of drift tubes in which they are switched on and off sequentially. This type of configuration is useful to study a narrow range of mobilities. Only the region containing the ions is switched on. In this way, ions under study are always subjected to a strong electric field, but the total voltage required remains limited. By doing this, very high resolutions can be achieved. The problem of this configuration is that only a very narrow range of mobility can be studied at a time. Only those ions hose drift time is synchronized with the on/off switching sequence can pass the filter. For some applications requiring a narrow band mobility filter this is not a problem. In fact, IMS devices have also been used as narrow band mobility filters by including a pulsed gate at the end of the drift tube. Only those ions hose drift time is synchronized with the offset time between the inlet and outlet gates can pass the IMS. Sequences of drift tubes and pulsed gates have also been used. However, these configurations produce a very low duty cycle, very poor transmission, and dilution of the ions when diffusion of the packet of ions is not compensated for.

The length of the IMS is also limited by the Brownian broadening of the ion packets in the transversal direction because ions are dispersed transversally, diluted, and eventually, they can be lost in the inner walls of the drift tube. Transversal diffusion can be counterbalanced by means of ion funnels. See U.S. Pat. No. 6,107,628. Various drift tubes can be coupled by synchronizing their gates producing a sequence of IMS to increase resolution of the mobility-filtered packets of ions. In order to counteract the dilution of the packets due to long drift times in long sequences, ion funnels can be also intercalated between the drift tube stages. This configuration also filters ions by synchronization between the residence time of an ion in the analyzer and the gates aperture offset time or the drifts tube switching on and off period. An interesting configuration of a sequence of gates, drift tubes, and ion funnels, was presented by D. Clemmer and colleagues, and termed High-Resolution Ion Cyclotron Mobility. See Ref [3]. In this configuration, ions are driven through a closed loop sequence of four drift tubes and four ion funnels. As the total electric potential difference has to be zero along a closed loop, they are forced to switch two of the drift tubes with an opposite field that pushes the ions backwards. This problem is easily overcome by using only two of the four drift tubes at a time and by changing the polarity of the system at a given frequency when the packs of selected ions are within the ions funnels. No gates are required in the loop because the two opposing drift tubes act themselves as gates. When the polarity changes in a drift tube, lagging ions, that could not reach the ion funnel in time, are chopped from the pack of ions. While overspeeding ions are stopped when they try to leave the ion funnel too early before the subsequent drift tube changes its polarity to push the ions favorably upwards.

Clemmer et al. explain that they accomplish filtration by changing the drift field at a frequency that is resonant with the ion's drift time through each region. Note that the selected ions are only affected by the favorable part of the cycle of the varying electric field that pushes the ions upwards in each stage of the cyclotron, while other ions are stopped by the unfavorable electric field. Selected ions are thus always subjected to a steady electric field as if they where traveling through a multistage drift tube with steady electric fields and far more than four drift tubes, ion funnels and gates. As a result, the output of filtered ions is pulsed as if a very long sequence of IMS was used to filter by means of gate synchronization.

IMS have been coupled with mass spectrometers, gas chromatography (GC), and liquid chromatography (LC). The IMS-MS technique produces tandem mass and mobility data which, as mentioned earlier, is useful for the analysis of complex samples and big molecules. Nevertheless, coupling an IMS with most commercial MS instruments is nontrivial because the IMS output is pulsed and generally takes place at low pressure, while most MS systems used in combination to LC sample steady (rather than pulsed) atmospheric pressure gases.

Two other devices have been used to separate ions carried in a gas, both producing steady beams of selected ions. These instruments are therefore more readily coupled with atmospheric pressure ionization mass spectrometers than drift time IMS. DMA: The first is the Differential Mobility Analyzers (DMA). In a DMA, a steady electric field and a steady laminar fluid velocity field are used. Different configurations have been proposed; see PCT/US2004/005133 U.S. Pat. Nos. 5,596,136 and 5,606,112 and Ref [4]. In the most common configuration, the flow moves in a channel where a perpendicular electric field is produced between two walls of the DMA channel. The ions are introduced continuously in the DMA through an inlet slit. The ions exhibit oblique trajectories as their velocity is the sum of the fluid velocity in one direction and the electric velocity in a different direction. According to their mobility, different ions have different trajectories. Only those ions within the selected narrow range of mobilities reach the DMA exit slit. This happens for a given fluid to electric velocity ratio which depends on the exact geometry of the DMA. A main difference between DMA and IMS is that the DMA produces spatial separation rather than time separation. The DMA is a narrow band filter, rather than a spectrometer. Once the fluid velocity is fixed, the filtered mobility can be selected by tuning the high voltage responsible for the electric field. Higher mobility ions require weaker electric fields while low mobility ions require stronger electric fields. Although the DMA is a narrow band filter, it is scannable, and therefore it can produce spectra. There are many types of DMA, cylindrical DMA have been widely used for the analysis of aerosols. However, it is difficult to access their inlet and outlet slits. For this reason it is difficult to couple cylindrical DMA with MS. Planar DMAs have more accessible inlet and outlet slits and have been coupled to several MS to produce two dimensional Mobility-Mass data. The main advantage of DMA-MS versus IMS-MS technique is that, once tuned at the mobility of interest, the DMA produces a steady flow of ions with a 100% duty cycle. Transmission and sensitivity is therefore much higher and synchronization with a MS is much simpler. See U.S. Pat. Nos. 5,869,831 and 5,936,242, and U.S. patent application Ser. No. 11/786/688 (PCT/EP2008/053762). The resolution achievable by a DMA is also limited by Brownian diffusion, but there are other factors affecting DMA resolution. Some details on the resolution of the DMA are required to provide the background of the present invention.

DMA resolution: If one assumes that the flow is perfectly laminar, the resolution in a DMA is limited by the Brownian diffusion and by the finite flow of ions. The limit given by Brownian diffusion can be broadly estimated as the characteristic length of the DMA channel 'L' divided by the diffusion broadening length given by $\sigma_r = \sqrt{2 \cdot D \cdot \tau}$, where D is the diffusion coefficient of the ions in the gas, and $\tau$ is the time spent by the ions in the DMA channel. On the other hand, at a given geometry and a given fluid velocity, the time spent by the ions in the DMA channel can also be broadly estimated as $\tau = L/V_f$. Joining the expressions for $\sigma$ and $\tau$, and the definition of the Reynolds number, yields a first rough expression for the resolution limit due to diffusion:

$$R_D = \sqrt{\frac{L \cdot V_f}{2 \cdot D}} = \sqrt{\frac{R_e \cdot v}{2 \cdot D}} \qquad (4)$$

where v is the kinematic viscosity of the drift gas. Equation 4 implies that the resolution increases with the Reynolds of the gas velocity field. The main problem arising in DMA is that, increasing the Reynolds to reduce diffusion effects, the flow of gas becomes unstable and resolution is spoiled by turbulence. DMA achieves satisfactory resolutions at low Reynolds that guarantee laminar flows when the diffusion coefficient D is low. Although it is difficult to achieve laminar flows at high Reynolds, a careful design can overcome this type of limitations. For instance, Martinez Lozano et al. have measured record resolutions above 100 [1/FWHM] for small ions of Tetra Heptil Ammonium Bromide (THABr$^+$) on a cylindrical DMA, and J. Rus and J. Fernandez de la Mora have made planar DMA coupled to several MS with which they have measured record resolutions up to 80 for the same THABr$^+$ ion.

These relatively high resolving powers are not easy to match, as the resolution of DMAs is strongly limited by turbulence, compressibility effects limiting the maximum velocity achievable, and sound pressure waves traveling upstream the DMA channel. Another problem regarding the DMA operation is that the pump required to produce the fast fluid flow in the DMA channel limits its operating temperature range and also hinders miniaturization. The DMA-MS technique also has the problem that it is difficult to deactivate the DMA and work in MS-only mode because there is an important offset between inlet and outlet slits.

FAIMS: Field Asymmetric Ion Mobility Spectrometry (FAIMS) is an alternative technique that, as the DMA, also separates ions geometrically rather than in time and, therefore, it also produces a continuous flow of selected ions with a 100% duty cycle. Moreover, FAIMS does not require a strong fluid velocity field, FAIMS has been successfully miniaturized, it has been successfully coupled to LC, GC and MS and, when coupled to an MS inlet, it is easy to deactivate and work in MS-only mode. FAIMS separates ions steadily in space according to weak nonlinearities associated to the slight dependence of their mobility on the strength of the electric field. In practice, mean ion trajectories are composed by the steady influence of a long lasting weak electric field (usually referred to as steady compensation voltage) and the small displacements due to many short opposed pulses of intense electric fields for which the ion mobility differs from that produced by the weak electric field. FAIMS therefore does not provide clearly interpretable structural information, as it separates not according to mobility, but according to slight nonlinearities in the mobility arising at high fields. See U.S. Pat. No. 5,420,424 and U.S. Pat. No. 6,806,466.

The main limitations of FAIMS are the need for a complex high voltage and high frequency (around 200 KHz) power supply, and, especially, its relatively low resolution compared to what can be achieved by drift time IMS or a DMA. Its main advantage is that, like the DMA, it can be coupled with many mass spectrometers having an atmospheric pressure interface.

In conclusion, there are presently no known solution to the related problem of achieving (i) a continuous, non-pulsed, narrow band ion mobility filter separating according to electrical mobility rather than according the non linear behavior of the mobility; (ii) operating at low flow Reynolds number (Re<5000) such that laminar and stable fluid movement is assured; (iii) achieving resolution higher than 40; (iv) being easy to couple to other analyzer equipments such as mass spectrometers (MS); (v) being easy to sidestep when coupled with other analyzer equipments such as MS in order to permit switching from Mobility-Mass measuring mode to simple Mass measuring mode.

SUMMARY OF THE INVENTION

The present invention provides a new way to select ions and charged particles according to their mobility. The new invention separates the ions in space by means of variable electric fields and, therefore, it produces a continuous output of filtered ions as in DMA. Yet, no high fluid velocity is required and all the problems associated with the high speed fluid flow are avoided. As the key for the separation of ions according to their mobility is the time-dependent electric field, the new invention will be termed Variable Electric Field Mobility Analyzer (VEFMA). The trajectories of the ions in a variable electric field are not steady along time and are not uniquely defined for a given mobility as in a DMA. Therefore, we should introduce the ion trajectory bundles concept (set of ion trajectories originating at the ion inlet, each at a different initial time relative to the origin of times for the applied voltage) rather than just ion trajectories depending on the mobility. However, under special circumstances, the ion trajectory bundle coalesces into a narrow region in space where these ions may be selectively collected. Only ions having the selected mobility have their trajectories coalescing in the VEFMA outlet and, thus, only said ions are efficiently transferred. Three preferred embodiments of the present invention are presented herein.

MORE DETAILED DESCRIPTION OF THE INVENTION

Figure 1:
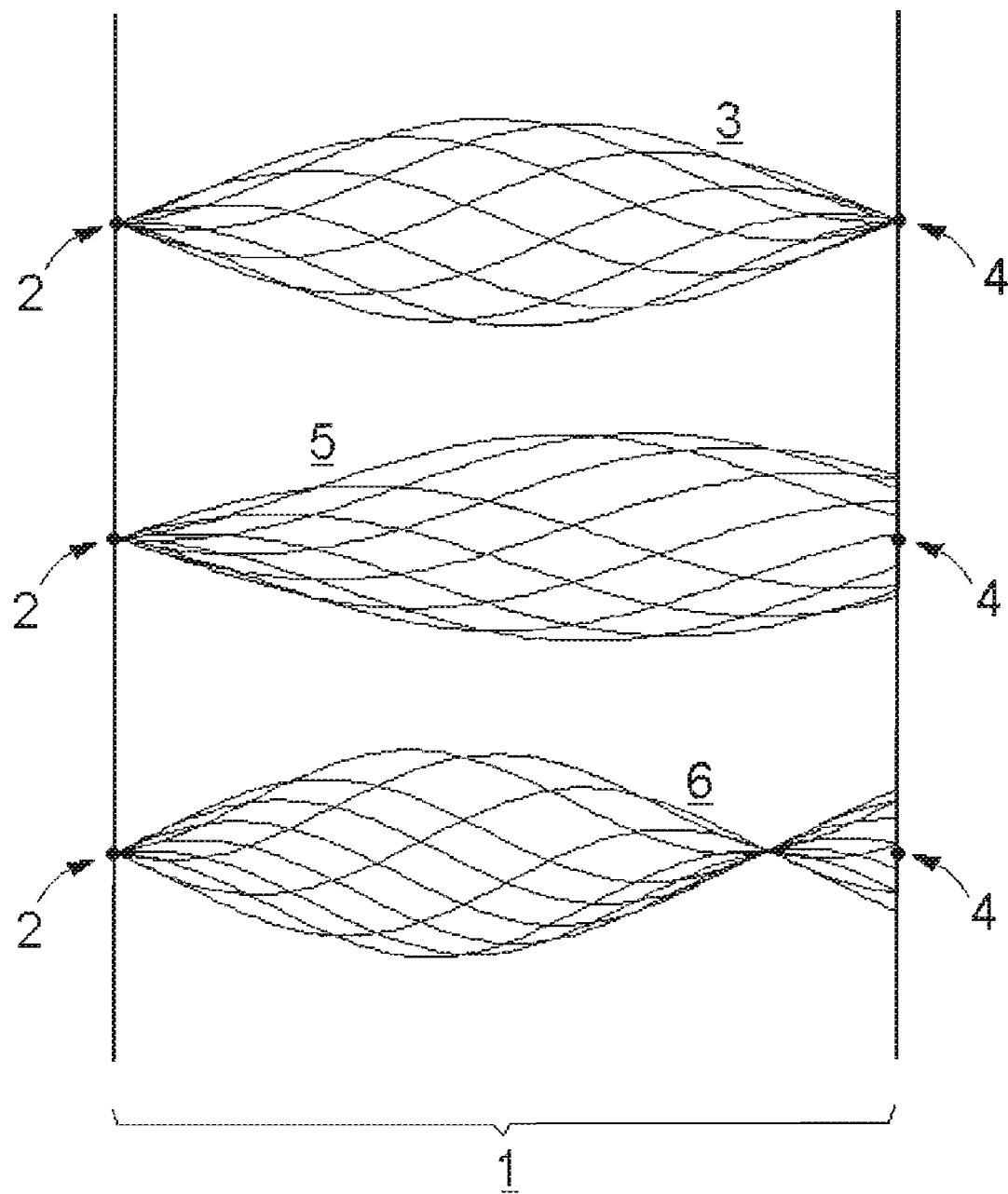
FIG. 1 illustrates schematically three different bundles of ion trajectories in an ideal Rotary VEFMA.

In a steady electric field, all ions follow the field lines and cannot therefore be separated in space. They can however be separated in time because they move with different speeds according to their mobility. This is indeed the phenomenon used in ion mobility spectrometers (IMS) of the time of flight type.

To separate the different ions from each other in space it is necessary to introduce a new variable that allows the shape of the ion trajectories to be dependent on the mobility of said ions. In a DMA the new variable is the fluid velocity. This can be more formally interpreted via dimensional analysis of the ordinary differential equations (ODEs) governing the movement in a DMA. The trajectories in a DMA depend on the electric to fluid speed ratio. The trajectories are uniquely defined for ions of a given mobility if ions entering the DMA through the same inlet. And therefore, ions can be geometrically separated according to said dimensionless ratio. The selected ions are those reaching the analyzer outlet. In a FAIMS system, this new variable is the field dependence of the mobility. Again, this can be more formally interpreted via dimensional analysis of the ODEs governing the movement of the ions.

In the method proposed in the present invention, the new variable enabling geometrical separation, and therefore steady mobility selection, is based on the use of variable electric fields with time-dependent field lines. In terms of the dimension analysis, the electric field can be expressed as $E = E_0 \cdot \bar{u}(x, \Omega t)$, where $\Omega^{-1}$ is the characteristic time of the variations of the electric field. Introducing this new expression in equation 2 as well as the dimensionless geometric and time variables $\bar{x}$ and $\tilde{t}$ (where $X = \bar{x} \cdot l$ and $$t = \tilde{t} \cdot \frac{l}{Z \cdot E_0}$$

yields:

$$\frac{d\bar{x}}{d\tilde{t}} = \bar{u}(\bar{x}, \tilde{t}\omega) \quad (5)$$

The new dimensionless parameter appearing in the Ordinary Differential Equation describing ion trajectories in time-dependent fields is:

$$\omega = \frac{\Omega \cdot l^2}{Z \cdot V} \quad (6)$$

Where $\Omega^{-1}$ is the characteristic time of the variations of the electric field, l is the characteristic size of the filtration device, V is the characteristic voltage applied (Note that $E_0 = V/l$), and Z is the mobility of the ion. Different ions with different values of Z will have different values of ω and thus will behave differently under the influence of a variable electric field. The parameter ω can be interpreted physically as the ratio between the residence time of an ion in the analyzer and the time for field variation.

According to equation 5, different ions with different mobilities will follow different trajectories if introduced though the same inlet in the region affected by the variable electric fields. Unlike in DMAs, trajectories are not uniquely defined for a given mobility because their shape also depends on the time at which ions enter said region affected by the variable electric fields (which states the initial condition to complete the Cauchy problem). However, a variety of schemes permit the continuous selection of one desired ion mobility at an outlet, for instance, when the position of the outlet is also time dependent and its movement is chosen to follow the trajectory of the desired ions. Separation is also possible with a fixed outlet in special configurations where the different trajectories of a selected mobility coalesce in a chosen region of the field during all or much of the cycle of the variable electric field. Selection is then achieved by collecting the ions in the coalescing region, which may, for instance, approximate a point (sampling orifice), or a curve (sampling slit). This configuration with a fixed collector and one coalescing mobility has certain advantages over other configurations, and will be pursued here in greater detail. But the invention includes the much wider range of situations where time dependent fields are used to select in space a narrow range of desired ion according to their mobility.

As the key for the separation of ions according to their mobility is the variable electric field, the present invention will be termed Variable Electric Field Mobility Analyzer (VEFMA). Filtration will take place when $\omega = \omega_0$. This circumstance can be also understood as synchronization between the residence time of an ion in the analyzer and the time for field variation.

Equivalent expressions to that of equation 6 could by defined for the FAIMS and for the IMS. For the method of the present invention, ω is typically of order unity and should in any case be smaller than 100. In contrast, ω is typically a much larger number in FAIMS devices.

An IMS system can also be used as a mobility filter. When working in spectrometer mode, the inlet gate is pulsed and produces packets of ions that are periodically introduced in the drift tube while the outlet gate remains always open. When working in filter mode, the outlet gate is also periodically opened and closed in such a manner that only a selected narrow band of the spectrum separated in the drift tube is transferred. The rest of the spectrum is chopped by the outlet gate. The offset time between inlet and outlet aperture determines the selected mobility. Selection is made based on the new dimensionless parameter:

$$\omega_{IMS} = \frac{\Omega_{IMS} \cdot l^2}{Z \cdot V} \quad (7)$$

which differs from the parameter ω given by equation 6 in the characteristic time utilized. The characteristic time $1/\Omega_{IMS}$ responsible for the filtration in an IMS is the offset time associated with the aperture of the gates, while the characteristic time $1/\Omega$ responsible for the filtration in a VEFMA is the time for field variation. This filtration can also be understood as synchronization between the residence time of an ion in the analyzer (the drift time of the ion) and the gates aperture offset time. The VEFMA is a far more efficient filter than this type of IMS filter as it can pass almost all ions of a given mobility, while this type of IMS filter is subjected to a well known low duty cycle.

In an IMS system, no matter what their mobility is, all ions travel approximately through the same trajectory near the axis of the drift tube. The difference in trajectories between selected and non selected ions can be only found in the gates where lagging and overspeeding ions are chopped from the pack of ions spread in the drift tube. The outlet signal of ions emerging from IMS based systems has to be pulsed because separation is produced in time. As a consequence of the pulsed output of ions, the duty cycle is small. In contrast, in a VEFMA, the trajectories of the different ions differ from each other because the whole electric field is varied in time. As the different ions are geometrically separated, the outlet of filtered ions can be smooth and continuous, and the duty cycle can be up to 100%.

Several different embodiments of the present invention comprising variable electric fields affecting the selected ions during a whole cycle can produce a continuous output of filtered ions and they are all included in the present invention.

The Rotary VEFMA: The Rotary VEFMA is one of the embodiments of the present invention of the type for which the trajectories of the ions of the selected mobility coalesce on a single point. The following discussion explains how an ideal Rotary VEFMA works. The conclusions of this discussion can be also applied for more complex and realistic configurations.

An ideal rotary VEFMA includes an axial and approximately steady electric field $E_0$ and an approximately perpendicular rotating electric field $E_1$. The angular velocity of the rotating field is $\Omega$. In order to facilitate the explanation of the behavior of the ions, a coordinate system is defined where the approximately steady electric field is established in the direction of the x axis, while rotary fields are established along the y and z axes. Ions will be introduced in the device through an inlet orifice located at the origin of the coordinate system.

An ion introduced in a gas at rest and subject to a steady axial field and a perpendicular rotary electric field will exhibit a helical trajectory.

The components of the electric velocity are given by:

$$u = Z \cdot E_0$$

$$v = Z \cdot E_1 \cdot \cos(\Omega \cdot t)$$

$$w = Z \cdot E_1 \cdot \sin(\Omega \cdot t) \qquad (8a, b, c)$$

Where u, v and w are, respectively, the x, y and z components of the velocity vector $V_E$, and t is the time.

The position of an ion introduced in the region affected by said electric fields through the inlet, at the point (x=y=z=0) at a time $t_0$ can be calculated by integration of equations 8 and is given by:

$$x = Z \cdot E_0 \cdot \Delta t \qquad (9a,b,c,d)$$

$$y = 2 \cdot \frac{1}{\Omega} \cdot Z \cdot E_1 \cdot \cos\left(\frac{\Omega \cdot (t + t_0)}{2}\right) \cdot \sin\left(\frac{\Omega \cdot \Delta t}{2}\right)$$

$$z = 2 \cdot \frac{1}{\Omega} \cdot Z \cdot E_1 \cdot \sin\left(\frac{\Omega \cdot (t + t_0)}{2}\right) \cdot \sin\left(\frac{\Omega \cdot \Delta t}{2}\right)$$

$$r = 2 \cdot \frac{1}{\Omega} \cdot Z \cdot E_1 \cdot \sin\left(\frac{\Omega \cdot \Delta t}{2}\right)$$

where $\Delta t = t - t_0$ is the time past since the ion entered through the inlet orifice, and $r = \sqrt{y^2 + z^2}$ is the distance of the ions to the x axis. Equation 9, uses the familiar expressions relating the sums and the products of sinusoidal functions.

An outlet orifice is placed aligned in the x axis at a distance l from the inlet orifice. The time required by the ions to travel the distance l along the x coordinate is $\tau$ and depends on the mobility of the ion. Basically, high mobility ions are faster and require smaller time than low mobility ions.

$$\tau = \frac{l}{Z \cdot E_0} \qquad (10)$$

FIG. 1 represents three types of ion trajectory bundles in an ideal Rotary VEFMA (1). Note that, though only a planar projection can be shown in the figure, the bundles are actually three dimensional and have axial symmetry. Ions enter in the Rotary VEFMA through the VEFMA inlet (2) at different times. First top bundle shown is the selected bundle of trajectories (3), having the trajectories coalescing at the VEFMA outlet (4), and corresponding to ions with the selected mobility. Second middle bundle shown is an overspeeding bundle of trajectories (5), corresponding to ions with higher mobility than the selected. And third bottom bundle shown is a lagging bundle of trajectories (6), corresponding to ions with lower mobility than the selected. Note that the singular coalescence or focusing phenomenon shown in the figure takes place for all trajectories within one period of field oscillation. Hence, if a mixture of ions is first introduced at time t=0 through the inlet of the device, complete separation of ions of the selected mobility is first achieved after one period of oscillation, and is continuously maintained thereafter. This behavior is in sharp contrast with the separation taking place in FAIMS, where very many periods of oscillation are required for ion separation, and even after thousands of such periods, a much weaker special confinement is achieved than that observed here.

The distance to the outlet orifice when the axial coordinate of the ions is X=l is easily calculated by composing equations 9d and 10, yielding:

$$R = 2 \cdot \frac{1}{\Omega} \cdot Z \cdot E_1 \cdot \sin\left(\frac{\Omega \cdot l}{2 \cdot Z \cdot E_0}\right) \qquad (11)$$

In an ideal case, only those ions having R=0 will reach the outlet orifice. Note that this can be achieved if:

$$\frac{\Omega \cdot l}{2 \cdot Z \cdot E_0} = n \cdot \pi \Leftrightarrow Z_n = \frac{\Omega \cdot l}{2 \cdot n \cdot \pi \cdot E_0} \qquad (12a,b)$$

Where n is any integer number. Note that equation 12a can be expressed in terms of the dimensionless parameter $\omega$, where $\omega$ satisfies $\omega = n \cdot \pi$. This condition can be explained as a synchronization of the characteristic time of the variable electric field and the time of residence of the ions in the VEFMA.

Equation 12b shows that not only a single mobility is selected by the VEFMA, but a family of them for every integer value of n. This problem can be solved, for instance, with an auxiliary high pass filter that separates the lower mobility ions given by n>1. In this case, the resolution of the auxiliary high pass filter has to be higher than 2 in order to effectively separate the mobility given by n=1 and the mobility given by n=2. Such a high pass filter is easily achieved and can be constructed, for instance, by a sheath flow of gas combined with an opposite electric field. In this configuration, low mobility ions are dragged backwards by the gas while high mobility ions are pushed forward by the electric field.

On the Theoretical Resolution of the Rotary VEFMA:

In order to estimate the resolution, it is necessary to estimate first the gain of the apparatus as a function of the Mobility. For a narrow band filter, said gain is zero or very low and comprises a peak around the selected narrow band. The narrower the peak, the higher the resolution.

As in other ion mobility filters, two main factors limit the resolution of the VEFMA. One is ion diffusion that broadens and mixes the ion trajectories. The other is the required sample flow rate. In order to produce non-zero sample flow rate of ions, infinitesimally thin trajectories are substituted by streak-tubes of ions of finite thickness. A finite streak-tube is produced at the VEFMA inlet and another finite streak-tube is sampled at the VEFMA outlet. For simplicity, the effects of Brownian broadening and finite streak-tubes are analyzed separately.

Figure 2:
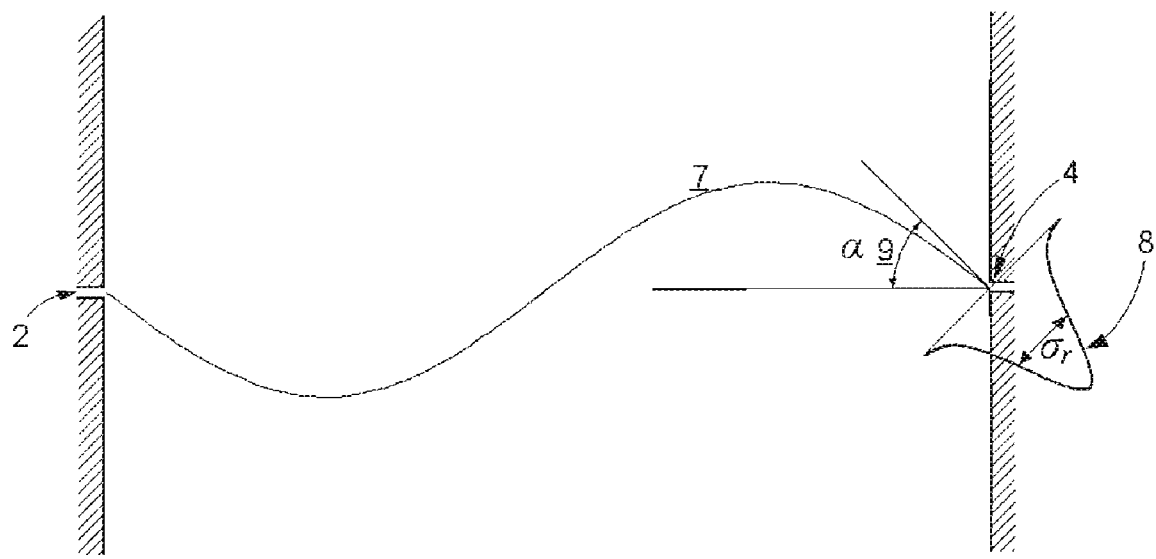
FIG. 2 illustrates a scheme of the concentration profile along a transversal section of an infinitesimally thin streakline of ions arriving at the VEFMA outlet, and the angle of arrival.

The Effect of Diffusion:

Assuming that the resolution is limited by diffusion, the streak-tubes based on the electric velocity can be considered infinitesimally thin. Therefore, the continuous flow of ions entering through the inlet produces, in first approximation, an infinitesimally thin streak-tube (a streak-line) filled with ions. The ion concentration gradient along the streak-line can be also neglected when compared with the ion concentration gradient measured transversally to the streak-line. The concentration profile at the inlet orifice is first considered a delta function centered in the origin. Under such a simplified conditions, and after a time $\tau$ has elapsed and diffusion has diluted the ions, the concentration profile perpendicular to the trajectory of the ions follows, approximately, a normal distribution with standard deviation $\sigma_r = \sqrt{2 \cdot D \cdot \tau}$ (where D is the diffusion coefficient of the ions through the medium). The streak-tube of ions also reaches the collection orifice at an angle $$\alpha = \arctan\left(\frac{\partial R}{\partial x}\bigg|_{R=0}\right); \frac{\partial R}{\partial x}\bigg|_{R=0} = \frac{E_1}{E_0}$$

with respect to the x axis. FIG. 2 shows schematically a streak-line (7) born in the VEFMA inlet (2), a Gaussian ion concentration profile (8) perpendicular to the streak-line, with standard deviation $\sigma_r$, and the angle $\alpha$ (9) at which the streak-line reaches the VEFMA outlet. Regarding the geometry of the trajectories, it is also interesting to use the maximum separation of the selected streak-lines to the axis. This maximum distance takes place at the middle of the ions trajectory. From equations 9 and 10, said maximum distance is:

$$R_{max} = \frac{E_1}{E_0} \cdot l \cdot \frac{1}{\pi} \quad (13)$$

Note that $\alpha$ can be expressed in terms of $R_{max}$.

For an infinitesimal flow rate of ions, the amount of ions exiting the VEFMA is proportional to the concentration of ions at the VEFMA outlet. On the other hand, the concentration of ions at the VEFMA outlet for a mobility close to the selected can be estimated as the ion concentration in a Gaussian profile of standard deviation $\sigma_r$ at a perpendicular distance to the streak-tube $R(Z) \cdot \cos(\alpha)$ where $R(Z)$ is given by equation 11. Linearizing the equations, and assuming that an ideal mixture of ions with uniform concentration distribution of mobility is introduced through the VEFMA inlet, the concentration of ions in the VEFMA outlet as a function of the mobility is a Gaussian function having a mean $Z_0$ (where $Z_0$ is the selected mobility as defined in equation 12 for n=1) and standard deviation given by:

$$\sigma_z = \sigma_r \cdot \frac{1}{\frac{\partial R}{\partial Z} \cdot \cos(\alpha)} \quad (14)$$

And, from equation 11, it follows that, at the selected mobility $Z_0$:

$$\frac{\partial R}{\partial Z}\bigg|_0 = \frac{E_1}{E_0} \cdot \frac{l}{Z_0} \quad (15)$$

Introducing the Stokes-Einstein relation $$D = Z \cdot \frac{k_B \cdot T}{e}$$

in the definition of $\sigma_r$, (where $k_B$ is Boltzmann's constant, T the absolute temperature of the gas, and e the charge on the ion), the above defined expression for the resolution for Gaussian distributions following the FWHM algorithm, the expressions for $\sigma_z$ and $Z_0$, and the geometric parameter $R_{max}$, the final expression for the resolution when it is limited by the diffusion $R_D$ is given by:

$$R_D = \sqrt{\frac{e}{k_B \cdot T} \cdot E_0 \cdot l} \cdot \frac{1}{4\sqrt{\ln(2)}} \cdot \frac{\pi \cdot \frac{R_{max}}{l}}{\sqrt{1 + \left(\pi \cdot \frac{R_{max}}{l}\right)^2}} \quad (16)$$

The Effect of Sample Flow Rate:

Assuming that the resolution is limited only by the finite flow rate extracted from the VEFMA through the VEFMA outlet, that the streak-tube extracted through the VEFMA outlet is approximately cylindrical having a radius $r_0$, and that the streak-line filled with ions introduced through the VEFMA inlet remains infinitesimally thin, ions will reach the VEFMA exit as long as the distance between the streak-line filled with ions and the extracted streak-tube is smaller than $r_0$. Said condition can be expressed as $R(Z) \cdot \cos(\alpha) < r_0$, where $R(Z)$ is given by equation 11. The gain function of the VEFMA as a function of the mobility follows a uniform distribution centered at $Z_0$. Again, linearizing the equations for the range of mobility close to the selected mobility allows simplifying the results. Under said simplification, the width of the uniform distribution is given by:

$$2 \cdot r_0 \cdot \frac{1}{\frac{\partial R}{\partial Z} \cdot \cos(\alpha)} \quad (17)$$

The parameter $r_0$ is related to the flow rate of ions through the expression $q = \pi \cdot r_0^2 \cdot Z \cdot \sqrt{E_0^2 + E_1^2}$ where q is the extracted ions flow rate. In order to better reflect the performances of the VEFMA, $r_0$ is substituted to show the impact of the flow rate q in the resolution $R_Q$ of the invention.

Using the expressions for the resolution under the FWHM algorithm for a uniform distribution, the expressions for the width of said uniform distribution and for $Z_0$, and the geometric parameter $R_{max}$, the final expression for the resolution when it is limited by the ion flow rate $R_Q$ is given by:

$$R_Q = \frac{\sqrt{\pi}}{2} \cdot \sqrt{\frac{l^2 \cdot E_0 \cdot Z}{q}} \cdot \frac{\pi \cdot \frac{R_{max}}{l}}{\left(1 + \left(\pi \cdot \frac{R_{max}}{l}\right)^2\right)^{1/4}} \quad (18)$$

In a more general case where both the extracted streak-tube and the ion filled streak-tube are not infinitesimally thin, $R_Q$ will be lower by a factor of approximately two, but one would expect that all the qualitative conclusions given by equation 18 will remain.

Equations 16 and 18 give a first criterion to design a Rotary VEFMA. The parameter $R_{max}/l$ should be as high as possible. Though, once this parameter is high enough, the improvement associated with further increases becomes negligible.

In a well balanced design, the limitations due to diffusion and flow rate should be of the same order. For a given design, the maximum flow rate achievable without impact on the resolution can be predicted by imposing $R_D = R_Q$. Below said maximum flow rate, the resolution will be unaffected by the flow rate as it is limited by Brownian diffusion and, over said flow rate, resolution will decay as flow rate is increased. At said limit, the resolution is given by equation 16 and the flow rate by:

$$q = l \cdot \frac{KT}{e} \cdot Z \cdot 4\pi \ln 2 \cdot \sqrt{1 + \left(\pi \cdot \frac{R_{max}}{l}\right)^2} \quad (19)$$

This implies that higher flow rates can always be achieved by using bigger apparatus. Note that the flow rate is proportional to the characteristic size l of the VEFMA. The resolution can be also increased by increasing $E_0 \cdot l = V$. The conclusion that bigger apparatus working with higher voltages can handle higher resolutions and higher flow rates is also valid for DMAs. But, in DMAs, high electric field strength and big apparatuses are associated with high Reynolds and Mach numbers which are limited by turbulence and compressibility effects. Unlike DMAs, in the present invention there is no limit in the resolution achievable because of high Reynolds and Mach numbers associated in DMA with high electric field strength and big apparatuses.

For instance, a Rotary VEFMA system working with V=100 kV voltage and l=10 cm in size can produce an ion flow rate of 0.15 lpm with a resolution of 500.

Figure 3:
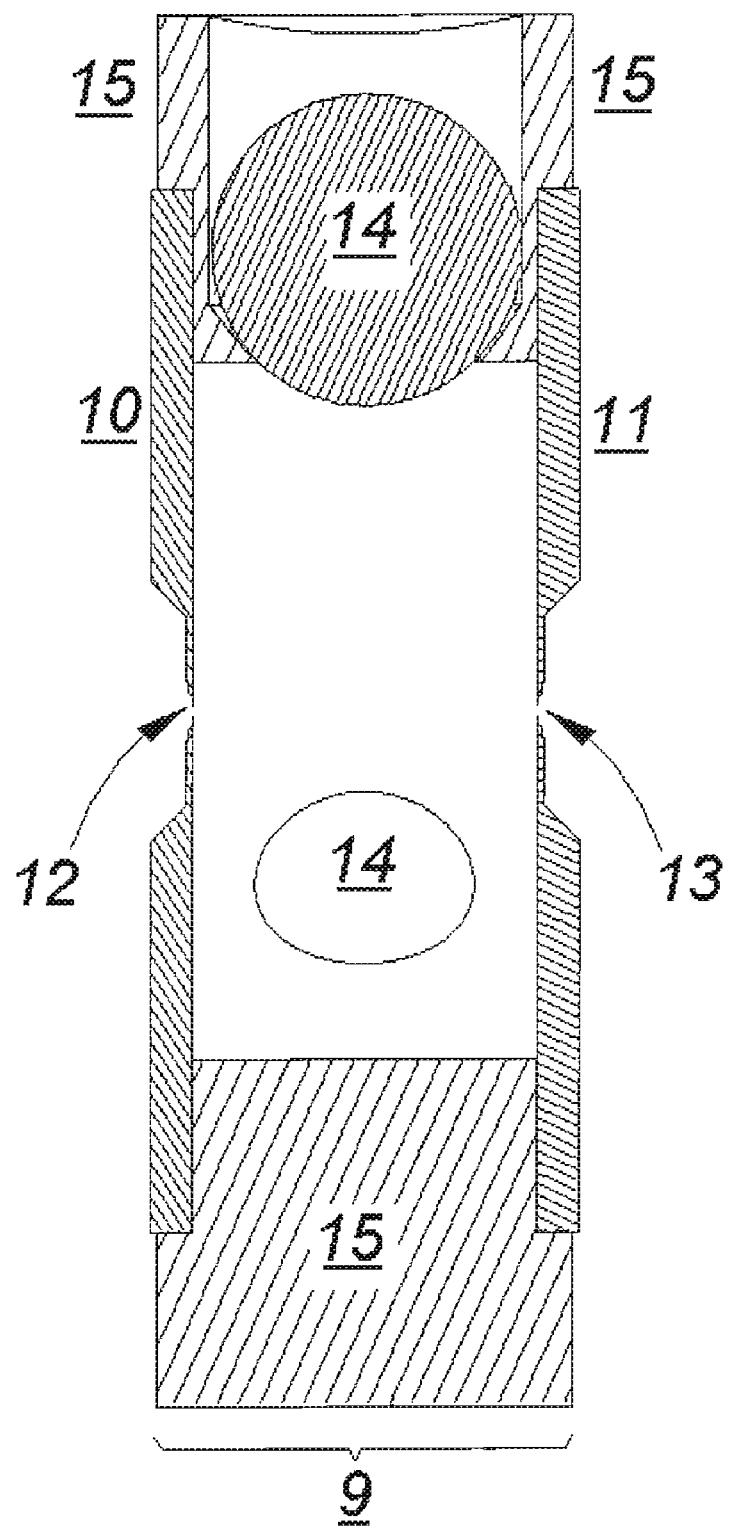
FIG. 3 illustrates a section view of the Electronic Rotary VEFMA.
Figure 4:
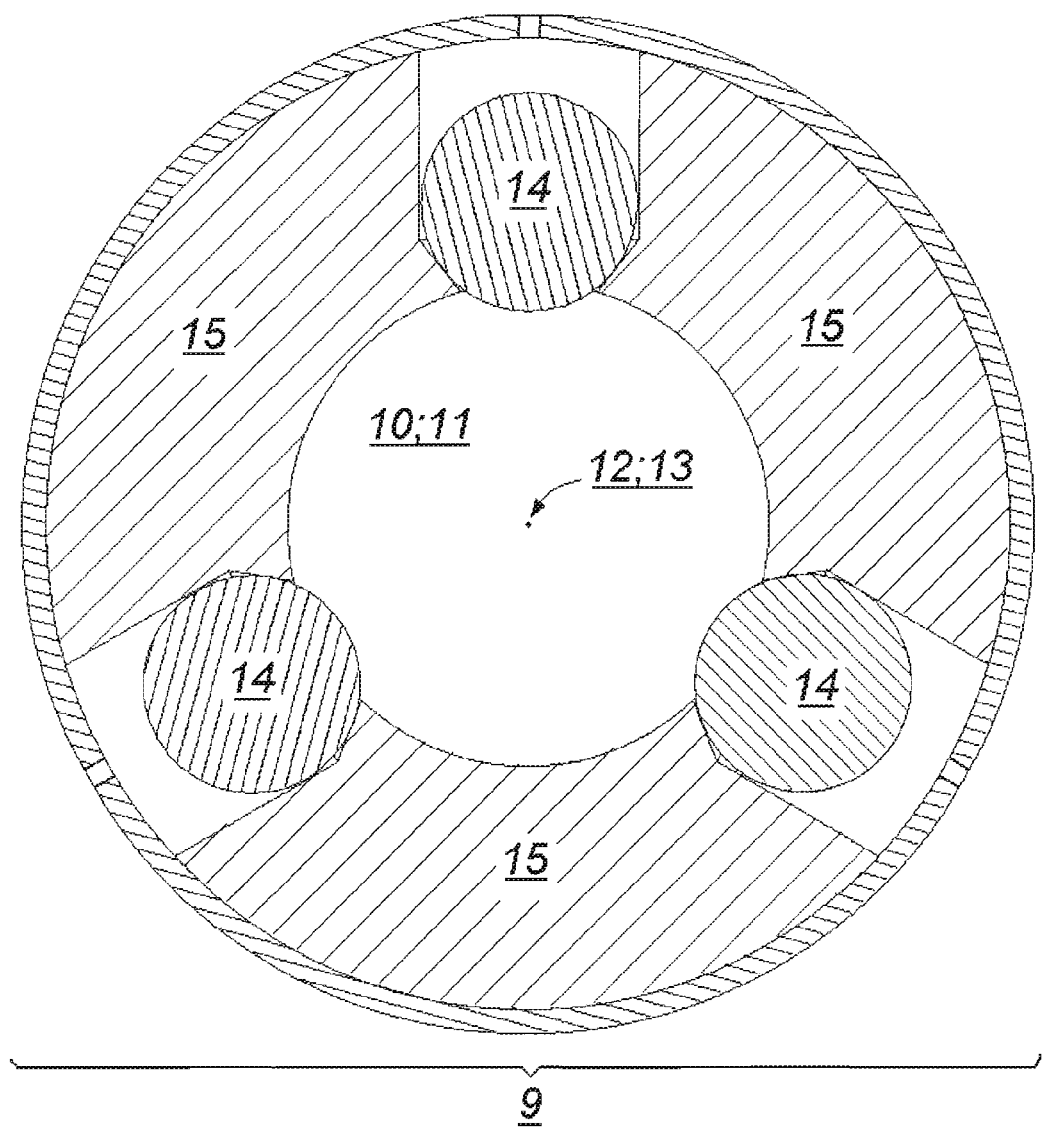
FIG. 4 illustrates a section view of the Electronic Rotary VEFMA having its axial direction aligned with the projection direction.
Figure 5:
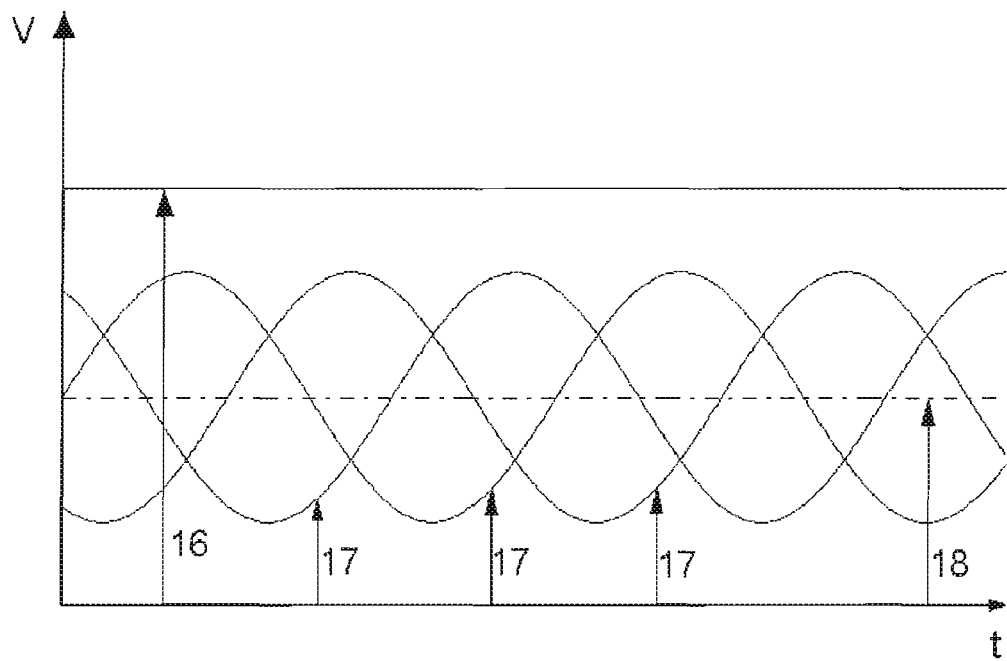
FIG. 5 illustrates schematically the voltage of the different electrodes of an Electronic Rotary VEFMA as a function of time.

The configuration above explained and analyzed is ideal and cannot be easily achieved. However, more complex and realistic electric field configurations can be subjected to the same principle of synchronization. A rotary electric field can be achieved by mechanically rotating a pair of deflectors, which may be in the form of electrodes, grids and/or semi-conducting surfaces. But it is much simpler and convenient to use multiple mechanically fixed electrodes or semi-conducting surfaces to produce an electronically rotating electric field. FIGS. 3 and 4 illustrate a preferred mechanical design of an Electronic Rotary VEFMA (9). FIG. 3 is a section view of the Electronic Rotary VEFMA. In this view, ions travel from left to right. FIG. 4 illustrates the Electronic Rotary VEFMA having its axial direction aligned with the projection direction. In this view, inlet and outlet are overlapped. The axial electric field is produced by means of two planar and parallel electrodes, these electrodes have been made planar to facilitate coupling this invention to other measuring devices like FAIMS or MS, but other different shapes can also produce suitable axial electric field and are therefore also a part of this invention. The first planar electrode is termed inlet electrode (10) and the second planar electrode is termed outlet electrode (11). Ions enter the Electronic Rotary VEFMA (9) through the inlet orifice (12) made in the inlet electrode (10). The VEFMA outlet is an outlet orifice (13) made in the outlet electrode aligned with the inlet orifice (12). The figure illustrates how these two orifices are drilled in a relatively thin metal plate, such that the axial electric field prevailing in the interior of the device can penetrate outside of the device and facilitate the entry of ions produced externally into the VEFMA. This process is conventionally facilitated by the additional use of external electrodes (not shown), also considered part of this invention. The thin plate orifice feature will not be emphasized in subsequent drawings, but its practical importance should not be underestimated. It is in fact necessary to keep the analyzing section of the instrument free from vapors, which would otherwise tend to attach to most ions, modifying their (dry) mobility, and complicating their identification. For this reason it is customary to protect the analyzing section of IMS and MS instrument from possible entry of humid or contaminated ambient air. This protection is often achieved by introducing clean gas into the analyzer, and letting this gas exit the analyzer through the ion inlet towards the open atmosphere. External ions that one wishes to analyze must therefore enter into the analyzer against this counterflow of clean gas, a task for which an external electric field driving the ions inwards is necessary. Although not shown in the figure, such common features of counterflow gas and external driving fields are also included in this invention. The axis of the rotary VEFMA is the line aligning the inlet orifice (12) and the outlet orifice (13). Ions are pushed towards the outlet electrode by the axial electric field which is produced by the voltage difference established between the inlet and the outlet electrode. The rotary field is produced by means of three spherical electrodes termed deflector electrodes (14) equally spaced and arranged in a circle contained in the plane equidistant to the inlet and outlet electrodes and centered in the axis of the rotary VEFMA. This embodiment of the invention comprises three spherical deflector electrodes for simplicity, but more deflector electrodes with different shapes could be also arranged to produce the electronically rotating field and are therefore also a part of this invention. Finally, insulators are required to separate the different electrodes. Insulators are also required to achieve a correct positioning of the electrodes. In the preferred embodiment of FIG. 3, the insulator (15) is a ring shaped piece able to accommodate the three deflector electrodes, the inlet electrode, and the outlet electrode. To electronically produce the rotary electric field, each deflector electrode has to be fed with a periodic wave of voltage. Each wave having an angular offset according to the geometrical angle of the deflector electrode. For example, the angular offset between the waves of a Electronic Rotary VEFMA having n deflector electrodes equally spaced should be 360°/n. FIG. 5 illustrates schematically the inlet electrode voltage (16) as a function of time and three deflector electrode voltages (17) as a function of time. Each deflector electrode voltage comprises a wave of frequency Ω and angular offset (phase shifts) of 360°/3=120°. If more than three deflector electrodes were used, more waves having equivalent angular offsets (360°/n) would be required. Sinusoidal waves are used for the preferred embodiment of the present invention, however, other wave shapes are also suitable to produce coalescing trajectories and, therefore, they are all a part of the present invention. A steady deflector electrode DC voltage (18) is superposed to the periodic voltages applied to the deflector electrodes. The value of this DC voltage (18) is half of the inlet electrode voltage. The deflection voltage is therefore the sum of said wave and said DC voltage. In the preferred embodiment of the invention, the outlet electrode is the reference for the voltage upon which other voltages are defined. Deflector electrodes, responsible for the rotary electric field, and inlet and outlet electrodes responsible for the axial electric field may partially shield each other. This effect would have a negative impact on the resolution since the deflection of trajectories would be reduced and the residence time, and thus diffusion, would be increased. In order to avoid shielding, the geometry has to be as simple as possible and the distances between different electrodes have to be well balanced.

Figure 6:
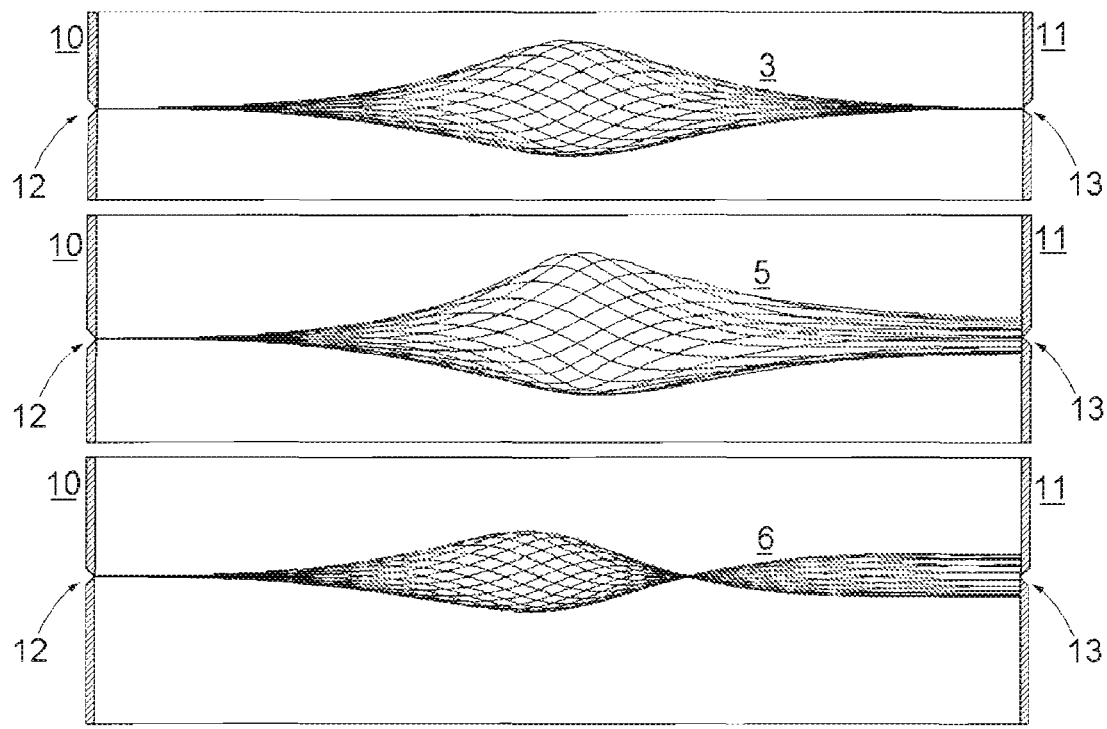
FIG. 6 illustrates schematically three different bundles of ion trajectories as numerically computed for an Electronic Rotary VEFMA.

FIG. 6 illustrates three types of ion trajectory bundles in an Electronically Rotary VEFMA (9) as computed numerically. FIG. 6 and FIG. 1 are equivalent; the difference is that trajectories of FIG. 6 are computed numerically for the real configuration described in FIGS. 3, 4 and 5. Note that though only a planar projection can be shown in the figure, the bundles are actually three dimensional. For simplicity, only the trajectories are represented. However, shielding effects can be observed. For instance, the ion trajectories emerge from the inlet orifice (12) perpendicularly to the inlet electrode (10), and reach the outlet electrode (11) also perpendicularly because these electrodes are equipotential and suppress completely the radial component of the rotary field. Ions enter in the Electronic Rotary VEFMA (9) through the inlet orifice (12) at different times. First top bundle shown is the selected bundle of trajectories (3), having the trajectories coalescing at the outlet orifice (13), and corresponding to ions with the selected mobility. Second middle bundle shown is an overspeeding bundle of trajectories (5), corresponding to ions with higher mobility than the selected. And third bottom bundle shown is a lagging bundle of trajectories (6), corresponding to ions with lower mobility than the selected. FIG. 6 demonstrates that synchronization of the characteristic time of the variable electric field and the time of residence of the ions in the VEFMA also produces coalescing trajectories for complex and real configurations. Notice that, also in this realistic case, only one period of oscillation of the field suffices for all ion trajectories to coalesce, and hence for steady ion separation to reach a steady state from then onwards. This drastic contrast with FAIMS is found in all the geometries we have studied, though in some cases two periods are necessary in a single VEFMA device. Other realistic electric field configurations can be subjected to the same principle of synchronization. In this way, the ions with selected mobility are first brought away from the axis, and then back to the axis right at the outlet orifice; while ions with different mobility will exhibit different trajectories that do not reach the collector orifice. Although the calculations of FIG. 6 have been performed for a situation with a symmetry plane, the figure shows that an axisymmetric electric field can focus underspeeding trajectories, suggesting that the existence of a plane of symmetry is not essential in axisymmetric devices. Consequently, this broader class of configurations where ions are selected by said principle of synchronization (with and without a symmetry plane) are all included in this invention.

The parameters used to control the selected mobility are the voltages and the frequency. At a given frequency, increasing the voltage increases the ion velocity and therefore ions with lower mobility are selected. At a given voltage, increasing the frequency lowers the characteristic time of the electric fields and faster ions having higher mobility are selected. In order to maximize the resolution, voltage should be as high as possible. In this circumstance, the frequency is the parameter which permits selecting the required mobility. The present invention is a narrow band mobility filter. But, by scanning over either the voltage or the frequency, it can be used as a scannable ion mobility spectrometer. The Rotary VEFMA can be coupled with other systems such a MS. If coupled at the inlet of an MS, by turning off the time variable electric field, but maintaining the axial electric field, different ions having different mobility entering through the inlet will reach the outlet orifice driven by the axial electric field. Therefore, filtration by mobility can also be deactivated if desired.

Equation 18 shows that the Rotary VEFMA is limited in its resolution by the low flow rate achievable and/or by the large sizes required to achieve flow rates appropriate for most modern atmospheric pressure source mass spectrometers (typically sampling 0.5 lpm or more). This limitation comes from the fact that resolution is inversely proportional to the square root of the sampled flow rate (proportional to $1/q^{1/2}$) because $r_0 \propto \sqrt{q}$ (where, as above defined, $r_0$ is the radius of the streaktube extracted through the outlet orifice). In planar geometries, involving slits instead of orifices, Resolution grows faster with $1/q$ because $r_0 \propto q$, where $r_0$ is now half the width of the extracted streak-tube in said two dimensional configuration. This permits the use of much smaller devices not limited in their resolution by the ions flow rate.

The 2D VEFMA: The two dimensional (2D) VEFMA is one of the embodiments of the present invention of the type for which the trajectories of the ions of the selected mobility coalesce on a single line. The following discussion explains how an ideal 2D VEFMA works. The conclusions of this discussion can be also applied to more complex and realistic configurations.

An ideal 2D VEFMA comprises an axial steady electric field $E_0$ and a perpendicular oscillating electric field $E_1$. The period of the perpendicular oscillating field is given by $2\pi/\Omega$. In order to facilitate the explanation of the behavior of the ions, a 2D coordinate system is defined where the x axis is parallel to the steady electric field and the y axis is parallel to the oscillating electric field. Ions will be introduced in the device through the inlet slit located at the origin of the coordinate system.

An ion introduced in a gas at rest and subjected to a steady axial field and a perpendicular oscillating electric field will exhibit a sinusoidal trajectory.

The components of the electric velocity are given by:

$$u = Z \cdot E_0$$

$$v = Z \cdot E_1 \cdot \sin(\Omega \cdot t) \tag{20a,b}$$

where u and v are, respectively, the x and y components of the velocity vector; and t is the time.

The position of an ion introduced in the region affected by said electric fields through the inlet slit (x=y=0) at a time $t_0$ can be calculated by integration of equations 20 and is given by:

$$x = Z \cdot E_0 \cdot (\Delta t) \tag{21a, b}$$

$$y = 2 \cdot \frac{1}{\Omega} \cdot Z \cdot E_1 \cdot \sin\left(\frac{\Omega \cdot (t + t_0)}{2}\right) \cdot \sin\left(\frac{\Omega \cdot \Delta t}{2}\right)$$

where $\Delta t = t - t_0$ is the time past since the ion entered through the inlet slit. Equation 21, uses the familiar expressions relating the sums and the products of sinusoidal functions An outlet slit is placed along the z axis at y=0, x=1. As for Rotary VEFMA, the time required by the ions to travel the distance l along the x coordinate is $\tau$, and depends on the mobility of the ion.

$$\tau = \frac{l}{Z \cdot E_0} \tag{22}$$

Figure 7:
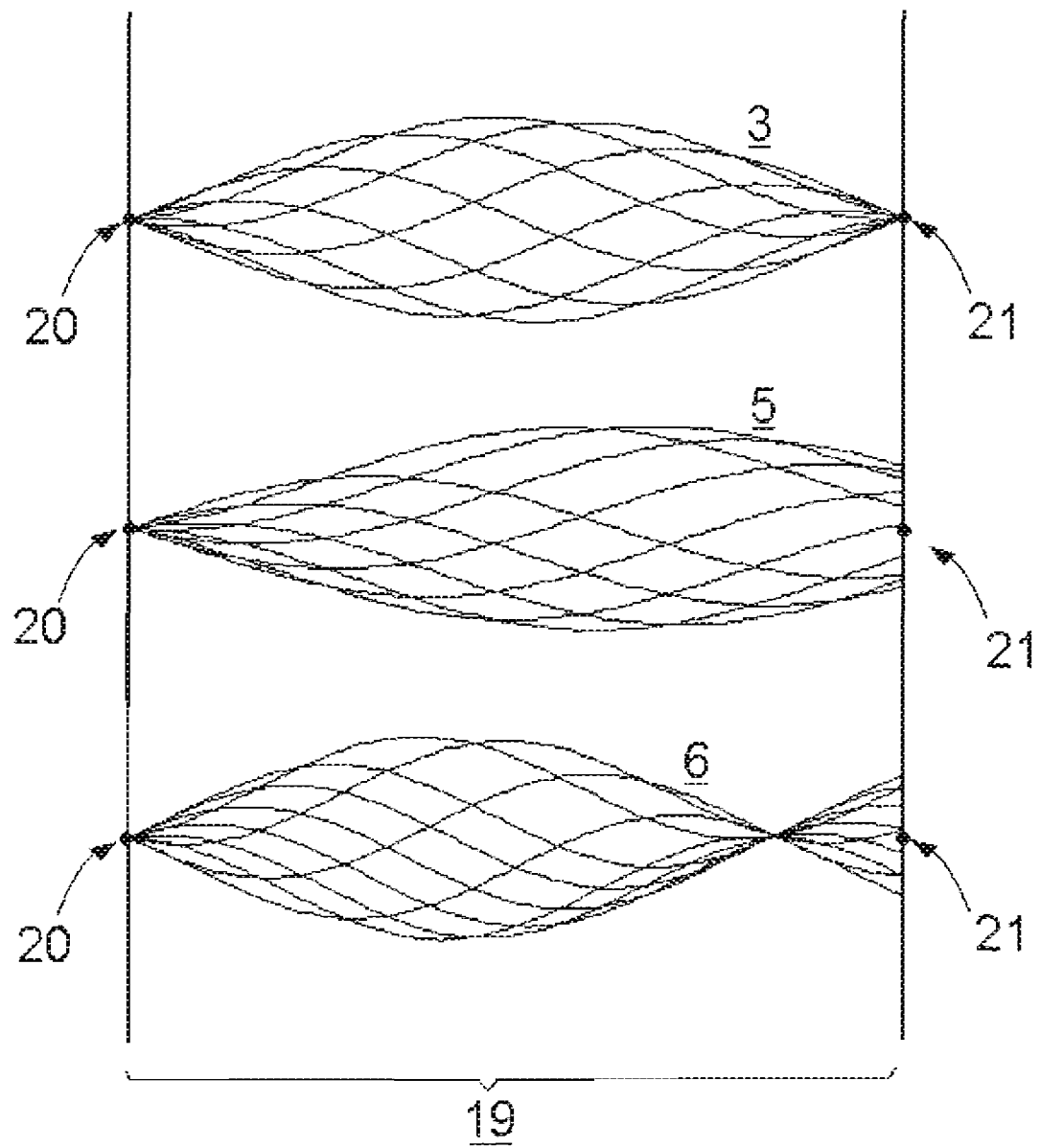
FIG. 7 illustrates schematically three different bundles of ion trajectories in an ideal 2D VEFMA.

FIG. 7 represents three types of ion trajectory bundles in an ideal 2D VEFMA (19). Ions enter in the 2D VEFMA through the VEFMA inlet slit (20) at different times. First top bundle shown is the selected bundle of trajectories (3), having the trajectories coalescing at the outlet slit (21), and corresponding to ions with the selected mobility. Second middle bundle shown is an overspeeding bundle of trajectories (5), corresponding to ions with higher mobility than the selected. And third bottom bundle shown is a lagging bundle of trajectories (6), corresponding to ions with lower mobility than the selected.

While for the Rotary VEFMA the distance of the trajectories to the outlet is constant, the trajectories in a 2D VEFMA are periodically intersecting the outlet. The distance to the outlet slit Y when the axial coordinate of the ions is x=l is easily calculated by composing equations 21b and 22:

$$Y = 2 \cdot \frac{1}{\Omega} \cdot Z \cdot E_1 \cdot \sin\left(\frac{\Omega \cdot l}{2 \cdot Z \cdot E_0}\right) \cdot \sin\left(\Omega \cdot t - \frac{\Omega \cdot l}{2 \cdot Z \cdot E_0}\right) \tag{23}$$

Note that, due to the time dependence of Y shown in equation 23, the different ions with different mobility will reach periodically the outlet slit and only the selected ions will produce a steady flow of ions. The condition to produce a steady flow of ions is the same equation 12 which, in terms of the dimensionless parameter $\omega$, can be expressed as $\omega = n \cdot \pi$. Note that this is the same equation required at the Rotary VEFMA. As well as in Rotary VEFMA, not only a single mobility is selected by the 2D VEFMA, but a family of them for every integer value of n. This problem can be solved, for instance, with an auxiliary high pass filter that separates the lower mobility ions given by n>1. In this case, the resolution of the auxiliary high pass filter has to be higher than 2 in order to effectively separate the mobility given by n=1 and the mobility given by n=2. Such a high pass filter is easily achieved and can be constructed, for instance, by a sheath flow of gas combined with an opposite electric field. In this configuration, low mobility ions are dragged backwards by the gas while high mobility ions are pushed forward by the electric field.

On the Theoretical Resolution of the 2D VEFMA:

As for the Rotary VEFMA, two main factors limit the resolution of the 2D VEFMA. One is ion diffusion that broadens and mixes the ion trajectories. The other is the required sample flow rate. The effect of Brownian diffusion in a 2D VEFMA is approximately the same as in the Rotary VEFMA. The main difference can be found in the effect of the sample flow rate. For simplicity, said effect is analyzed assuming that the effect of Brownian diffusion on the resolution is negligible.

To estimate the resolution it is first necessary to estimate the gain of the apparatus as a function of the mobility. Assuming that the resolution is limited only by the finite flow rate extracted from the VEFMA through the outlet slit, that ions at x=1 and having $|y|<\delta Y$ are sampled by the outlet slit, and that the streak-line filled with ions introduced through the inlet slit remains infinitesimally thin, ions will reach the VEFMA exit as long as $|Y|<\delta Y$, where Y is the distance to the outlet slit given by equation 23, and $\delta Y$ is the height of the sampled streak-tube which is proportional to the ion flow rate. The output of a single 2D VEFMA will be pulsed for those ions not selected, and continuous for the selected mobility. During the time when $|Y|<\delta Y$, the ions will be transferred. Said pulsed signal can be characterized by a Pulse Repetition Interval (PRI) and a Pulse Width (PW). Introducing the expression Y(t) from equation 23, said PRI and PW are given by:

$$PW = \frac{2}{\Omega} \arcsin\left(\frac{\delta Y}{l} \cdot \frac{E_0}{E_1} \cdot \frac{1}{\frac{2E_0 Z}{\Omega l} \cdot \sin\left(\frac{\Omega l}{2E_0 Z}\right)}\right) \tag{24a, b}$$

$$PRI = \frac{\pi}{\Omega}$$

In average, the gain of transferred ions can by computed as s=PW/PRI. This ratio depends on the mobility and is equal to one for the selected mobility and for a narrow range of mobility around the selected. The function s can be further simplified using the dimensionless parameters $$k = \left(\frac{\delta Y}{l} \cdot \frac{E_0}{E_1}\right)^{-1}$$

and $$\omega = \frac{\Omega \cdot l^2}{2 \cdot Z \cdot V} = \frac{\Omega \cdot l}{2 \cdot Z \cdot E_0}$$

yielding:

$$s = \frac{2}{\pi} \arcsin\left(k^{-1} \cdot \frac{\omega}{\sin(\omega)}\right) \tag{25}$$

Figure 8:
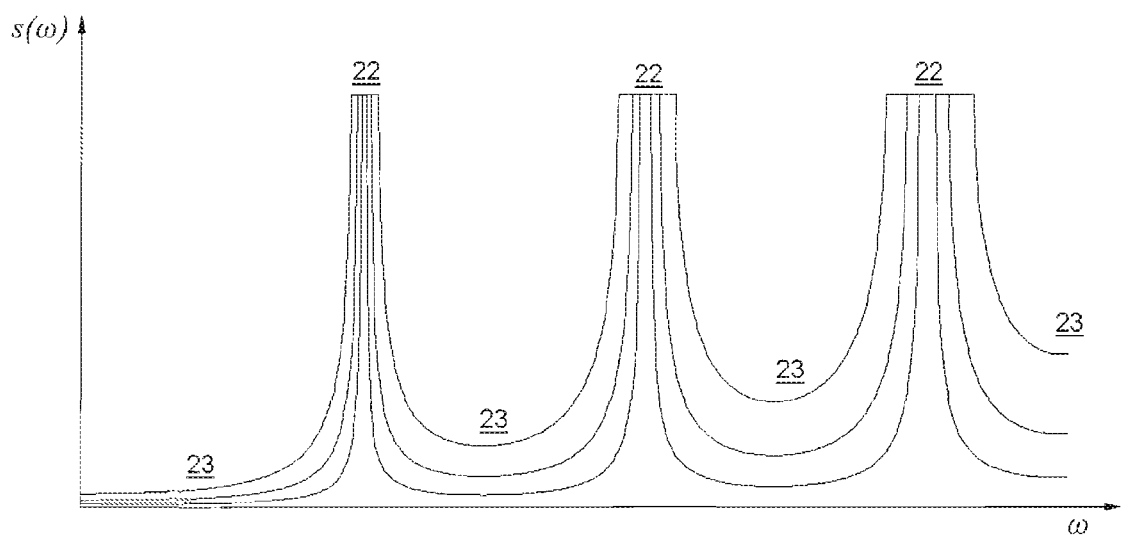
FIG. 8 illustrates the gain of a 2D VEFMA as a function of the dimensionless parameter ω for three different values of the dimensionless parameter k (equation 25).

FIG. 8 illustrates the function $s(\omega)$ for three different values of k. Showing the first three peaks (22) corresponding to the first three resonances (for $\omega = n \cdot \pi$; n=1, 2, 3, ... ). The function $s(\omega)$ can be interpreted as the gain of the 2D VEFMA for a given ion as a function of the dimensionless frequency of the oscillating electric field. Resolution for the first peak appearing in FIG. 8 has been numerically computed using the FWHM algorithm for various values of k. The numerical computations show that resolution is linear with the parameter k and is approximately given by:

$$R_Q \approx 0.353 \cdot k \tag{26}$$

On the other hand, the height of the sampled streak-tube is, as above mentioned, related to the sampled ions flow through the expression $q = 2 \cdot \delta Y \cdot L \cdot Z \cdot E_0$ where L is the length of the slit. Introducing the definitions for k and $\delta Y$ in equation 26, the resolution can be expressed as:

$$R_Q \approx 0.353 \cdot \frac{E_1}{E_0} \cdot \frac{2l \cdot E_0 \cdot Z}{q/L} \tag{27}$$

where q/L is the flow rate per unit of slit length.

Comparing equations 18 and 27 it can be seen that the 2D VEFMA produces much higher resolutions with lower device sizes than rotary VEFMA. For instance, for $E_0Z=100$ m/s; $l=10$ cm, $E_1=E_0$; $R_{max}=1/\pi$; $L=1$ cm; and $q=4$ lpm; the equation 27 for the 2D VEFMA provides $R_Q=1059$ while the equation 18 for the Rotary VEFMA provides only $R_Q=77$.

In return, though the resolution produced by the 2D VEFMA is much higher, the total amount of undesired ions is lower in the rotary VEFMA than in the 2D VEFMA. Note that the function $s(\omega)$ shown in FIG. 8 also shows a non zero gain for values of $\omega$ far from the peaks (23). This non-zero average signal is produced by the above mentioned pulsed signal of non desired ions and is therefore considered to be noise. Said noise produced by the pulsed undesired signal can be a disadvantage for this configuration. However, said noise follows a known non-random pulsed pattern and can be post-processed as long as the detector sensing the ions exiting trough the outlet slit is fast enough to capture the signal time variation. Furthermore, said pulsed signal can be used to get the complete mobility spectrum while a preferential mobility is also selected. Note that equation 23 also states that the time at which the pulses are produced (when $Y=0$) depends on the mobility of the ions. Another means to drastically reduce the noise of the 2D VEFMA is using two stages of 2D VEFMA. Multistage VEFMA is another embodiment of the present invention and will be studied later in the text with more detail.

Figure 9:
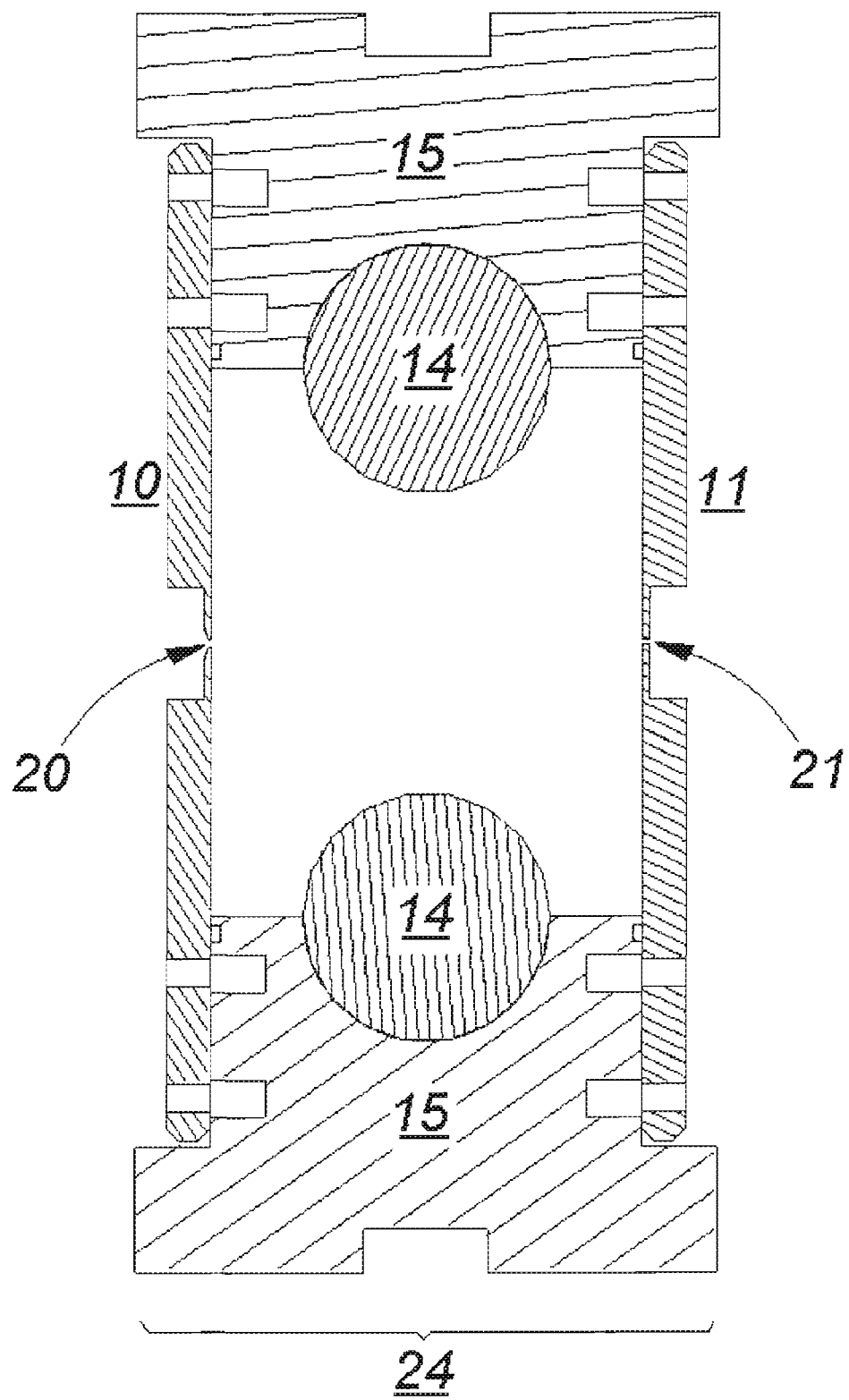
FIG. 9 illustrates a section view of the 2D VEFMA.
Figure 10:
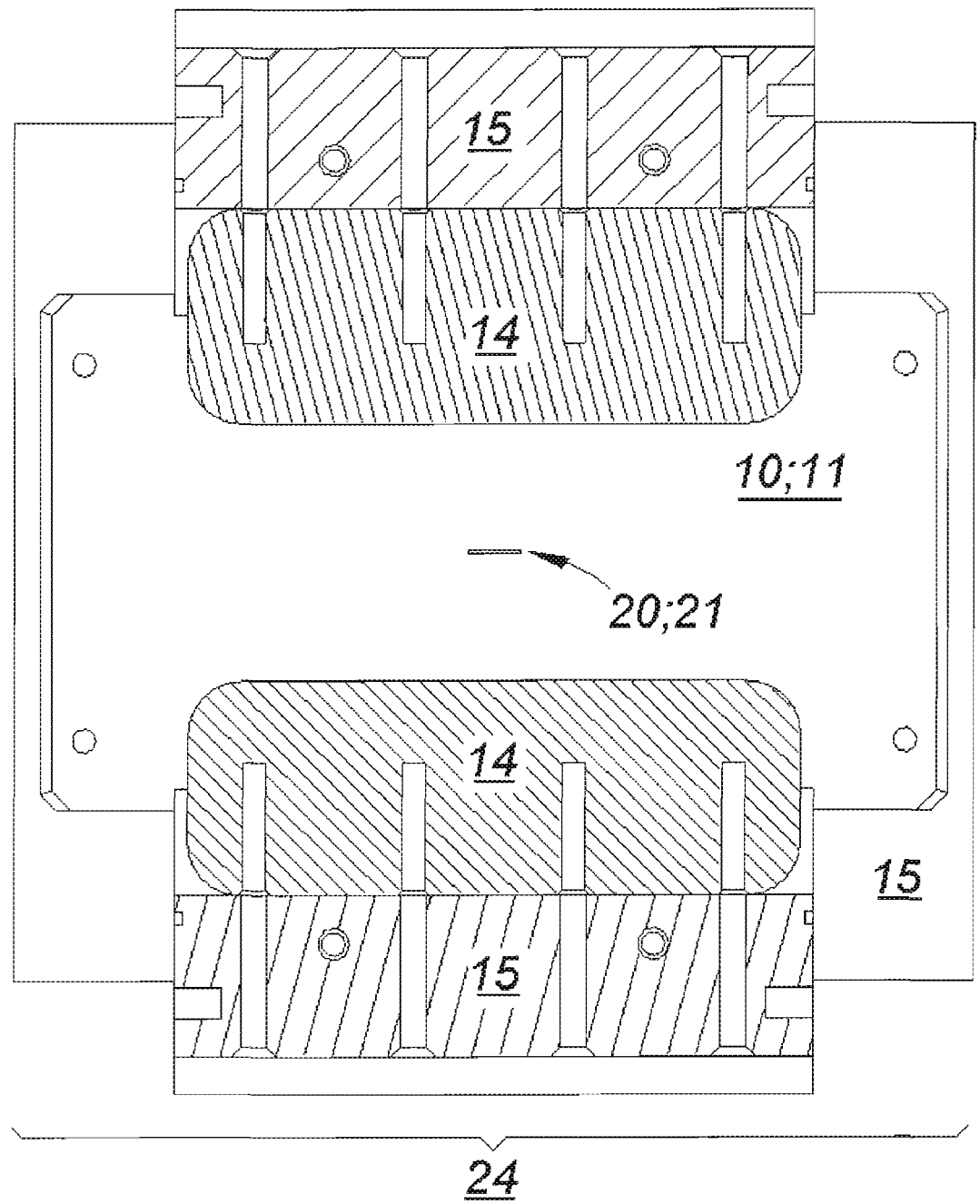
FIG. 10 illustrates a section view of the 2 VEFMA having its axial direction aligned with the projection direction.

Again, achieving uniform electric fields is a complicated and unnecessary task. The idealized fields assumed in the ideal analysis are useful to understand the behaviour of a 2D VEFMA, but other configurations of electric fields, electrodes, meshes, semi-conducting surfaces and dielectric parts also produce the required effect of focusing the different trajectories in the same region for a selected mobility. A more realistic field configuration, symmetrical but not uniform, is achieved in the embodiment of the 2D VEFMA shown in FIGS. 9 and 10. FIG. 9 is a section view of the 2D VEFMA (24). In this view, ions travel from left to right. FIG. 10 illustrates the 2D VEFMA having its axial direction aligned with the projection direction. In this view, inlet and outlet slits are overlapped. The axial electric field is produced by means of two planar and parallel deflectors, which may be in the form of electrodes, grids and/or semiconducting surfaces. Preferably, the deflectors are in the form of electrodes; more preferably, these electrodes have been made planar to facilitate coupling this invention to other measuring devices like FAIMS or MS, or to another VEFMA stage, but other different shapes can also produce suitable axial electric field and are therefore also a part of this invention. The first planar electrode is termed inlet electrode (10) and the second planar electrode is termed outlet electrode (11). Ions enter the 2D VEFMA (24) through the inlet slit (20) made in the inlet electrode (10). The VEFMA outlet is an outlet slit (21) made in the outlet electrode (11) aligned with the inlet slit (20). The axis of the 2D VEFMA is the line aligning the inlet slit (20) and the outlet slit (21). Ions are pushed towards the outlet electrode by the axial electric field which is produced by the voltage established between the inlet and the outlet electrodes. The oscillating electric field is produced by means of two electrodes termed deflector electrodes (14) located symmetrically between the inlet and the outlet electrodes. For this embodiment of the invention, two cylindrical deflector electrodes are used, but other shapes, including an even number of electrodes or semi-conducting surfaces can also produce the required electric field and they are also a part of this invention. Finally, insulators are required to separate the different electrodes. Insulators are also required to achieve a correct positioning of the electrodes. In the preferred embodiment of FIG. 9, the insulator (15) is a box shaped piece dimensioned to accommodate the two deflector electrodes, the inlet electrode, and the outlet electrode. As in the Electronic Rotary VEFMA, the distances between electrodes have to be well balanced to mitigate self shielding effects.

Figure 11:
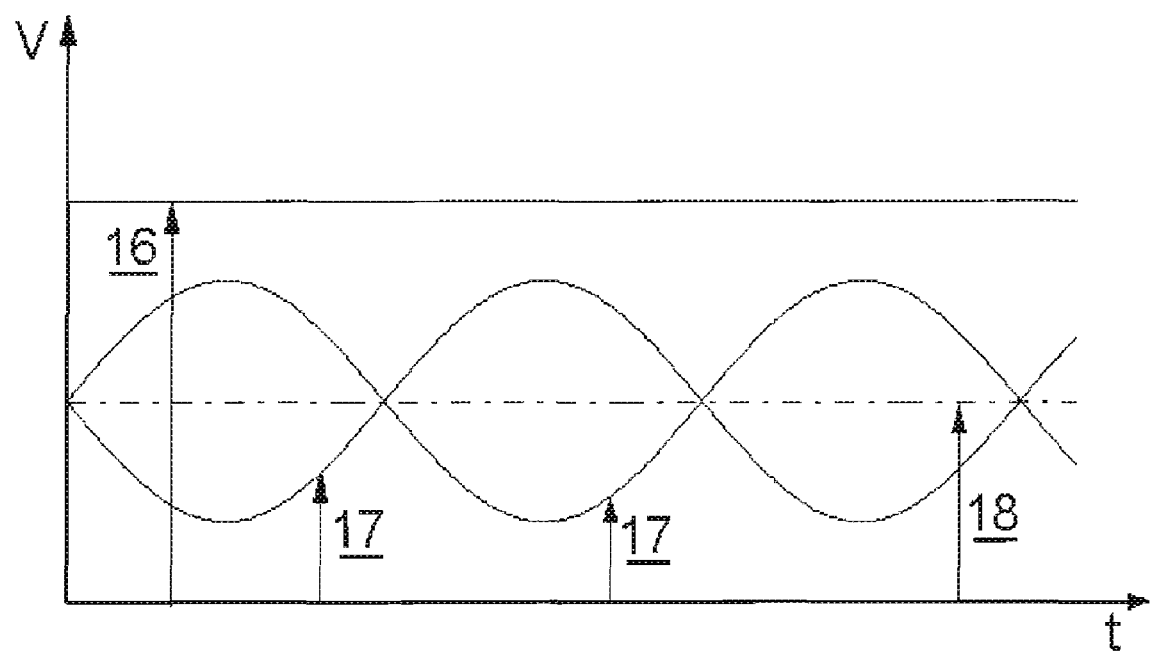
FIG. 11 illustrates schematically the voltage of the different electrodes of a 2D VEFMA as a function of time.

FIG. 11 illustrates schematically the inlet electrode voltage (16) as a function of time and the two deflector electrode voltages (17) as a function of time. Each deflector electrode voltage comprises a wave of frequency $\Omega$ and a DC level. The two waves for the two deflector electrodes are opposed to each other to produce the oscillating field. Sinusoidal waves are used for the preferred embodiment of the present invention, however, other wave shapes are also suitable to produce coalescing trajectories and, therefore they are all a part of the present invention. Upon said wave responsible for the oscillating electric field, a steady deflector electrode DC voltage (18) has to be applied to the deflector electrodes, The value of this DC voltage (18) is half of the inlet electrode voltage so that the axial electric field is symmetrical at both sides of the deflector electrodes. The deflection voltage is therefore the sum of said wave and said DC voltage. In the preferred embodiment of the invention, the outlet electrode is the reference for the voltage upon which other voltages are defined.

Figure 12:
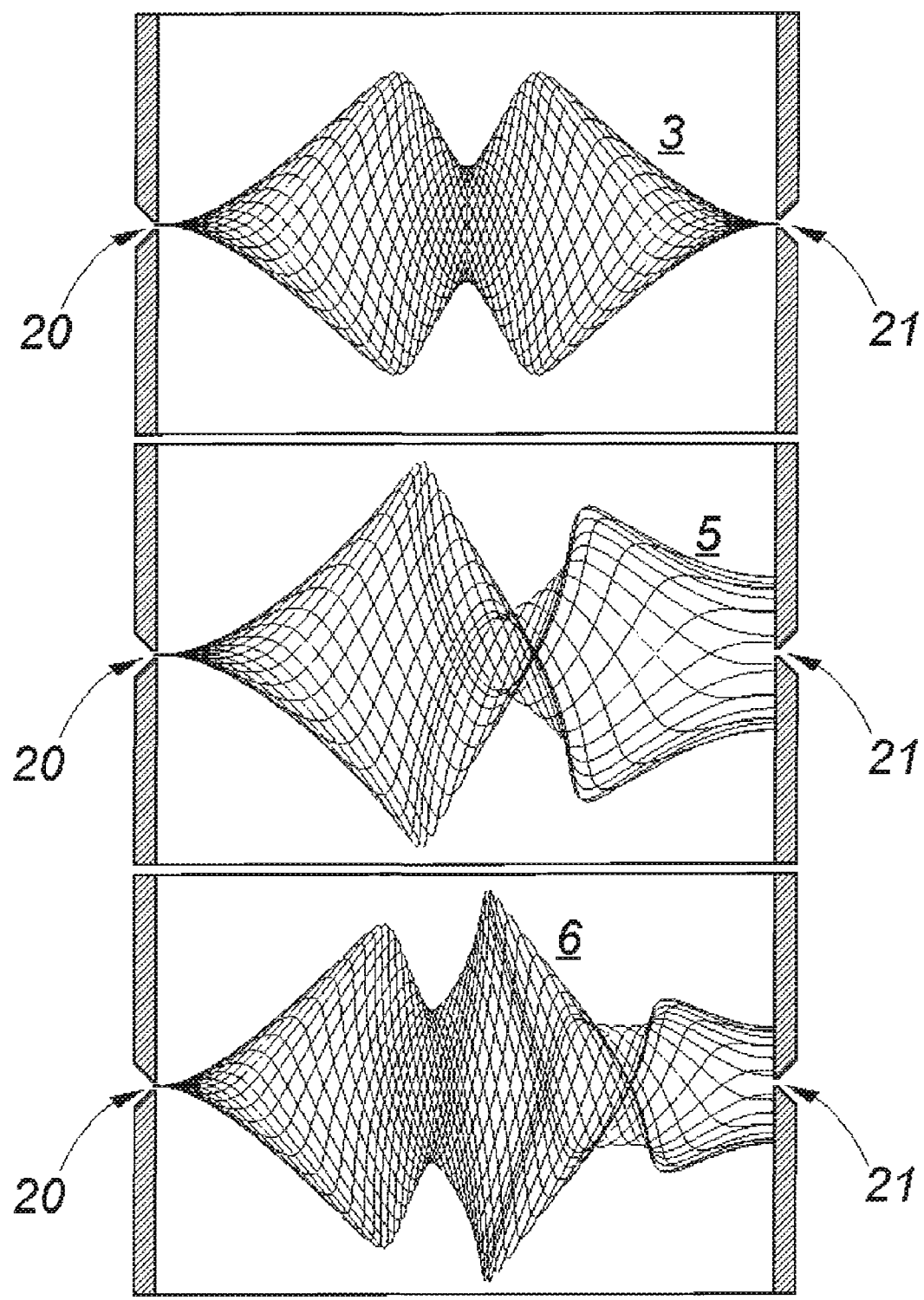
FIG. 12 illustrates schematically three different bundles of ion trajectories as numerically computed for 2D VEFMA.

FIG. 12 illustrates three types of ion trajectory bundles in a 2D VEFMA (24) as computed numerically. FIG. 12 and FIG. 7 are equivalent; the difference is that trajectories of FIG. 12 are computed numerically for the real configuration described in FIGS. 9, 10 and 11. Ions enter in the 2D VEFMA (24) through the inlet slit (20) at different times. The first top bundle shown is the selected bundle of trajectories (3), having the trajectories coalescing at the outlet slit (21), and corresponding to ions with the selected mobility. The second middle bundle shown is an overspeeding bundle of trajectories (5), corresponding to ions with higher mobility than the selected value. And the third bottom bundle shown is a lagging bundle of trajectories (6), corresponding to ions with lower mobility than the selected value. FIG. 12 proves again that synchronization of the characteristic time of the variable electric field and the time of residence of the ions in the VEFMA also produces coalescing trajectories for complex and real configurations, at least when they have a symmetry plane. Note that, though the overspeeding (5) and underspeeding (6) trajectories do partially focus on the axis in the realistic geometry, they present a strong aberration effect (many trajectories are focused, but not all), while they do focus perfectly in the idealized situation depicted in FIG. 7. The main difference between both cases is that the uniform field in the ideal problem is symmetric with respect to all planes normal to the axis, while the real field in the real geometry only has one plane of symmetry. Since the trajectories that do focus best are those whose special mobility makes them symmetric with respect to that unique symmetry plane of the field, it is clear that a high level of geometrical symmetry is useful to maximize the resolution of this 2D device. Other realistic 2D electric field configurations can be subjected to the same principle of synchronization. For this, it is often convenient to arrange both oscillating and axial fields symmetrically with respect to a plane symmetrically located in between the VEFMA inlet and the VEFMA outlet. In this way, the ions with the selected mobility are preferably first brought away from the axis, and then back to the axis right at the outlet orifice. In contrast, ions with different mobilities will exhibit different and non symmetrical trajectories that do not reach the collector orifice. Said configurations select ions by said principle of synchronization and are therefore a part of this invention.

There are other limitations regarding the resolution of the VEFMA. For instance, the quality of the high voltage waves can change the ion trajectories introducing noise and reducing the resolution. The shape of said waves will also have an impact on the final resolution of the apparatus. Different wave shapes can be utilized to feed the VEFMA. This can be easily demonstrated mathematically at least in the case of anti-symmetric waves and uniform electric fields. A generic anti-symmetrical evolution of the electric field (termed also wave for simplicity) can be expressed as:

$$E_g(t) = \sum_{i=1}^{\infty} A_i \cdot \sin(i \cdot \Omega \cdot t) \qquad (28)$$

Where i is an integer number. Combining equations 12 and 28 leads to a new criterion for the selected mobility given by:

$$Z = \frac{i \cdot \Omega \cdot l}{2 \cdot n \cdot \pi \cdot E_0} \qquad (29)$$

Figure 13:
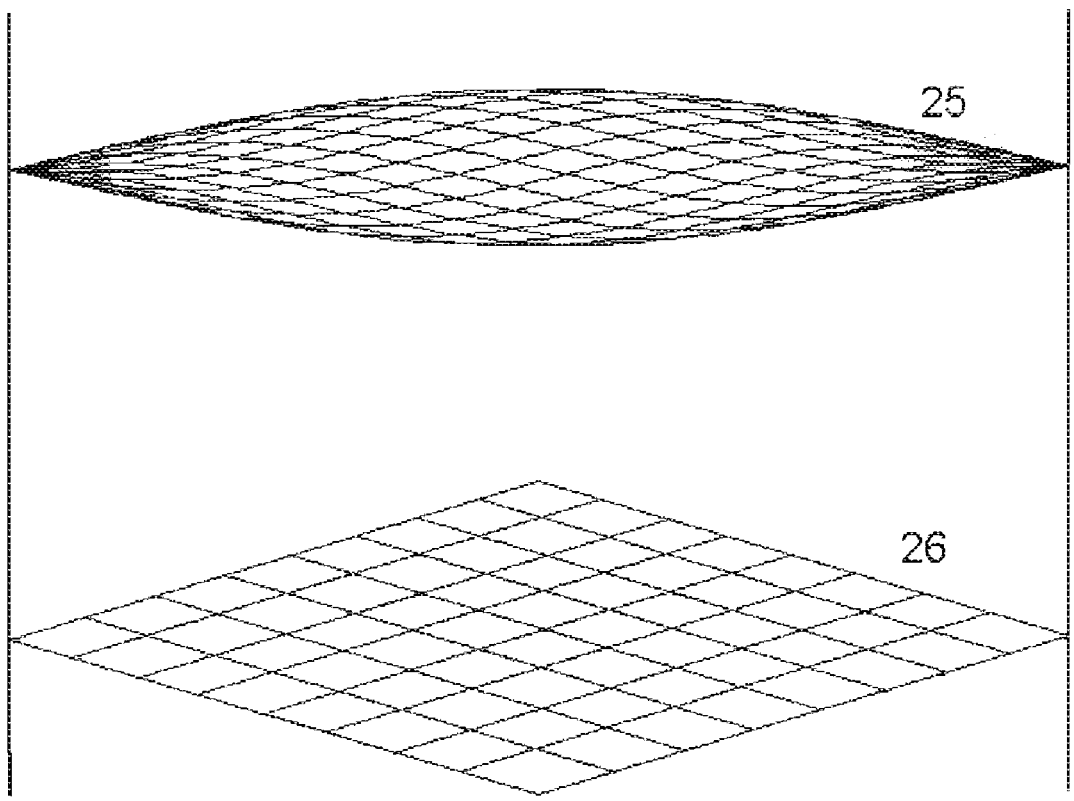
FIG. 13 illustrates schematically two bundles of ion trajectories of the selected ions in a 2D VEFMA under the effect of a sinusoidal varying field and a square wave varying field.

If equation 29 is satisfied for i=1 and n=1 and for a given value of Z, then it can be also satisfied for the same value of Z and for every harmonic of the wave defined by the parameters i and $A_i$ in equation 29 as long as i=n and thus, it is proven that the same mobility will be selected for any antisymmetric waveform in a uniform electric field. This can be more intuitively explained with the following reasoning: If the first harmonic is synchronized having one full cycle, the second harmonic will be synchronized having time for two cycles, the third harmonic will have three cycles, and so on. This is possible because, as above mentioned, synchronization occurs for multiple resonances ($\omega = \pi \cdot n$). To illustrate this, FIG. 13 represents two bundles of ion trajectories in an ideal 2D VEFMA. An ideal sinusoidal wave produces the upper bundle (25) and an ideal square wave produces the lower bundle (26). Note that, though this demonstration has been limited to the case of uniform fields and anti-symmetric waves, the invention is not limited to such restricted conditions. Other configurations having non uniform electric fields and non anti-symmetric waves can produce coalescing ion trajectory bundles.

The analysis of the trajectories of the ions and the resolution of a VEFMA has been so far been limited to the case in which the evolution of the electric fields is sinusoidal. As explained above, other different wave shapes can be used in a VEFMA and consequently they all are part of the present invention. For instance, the behavior of a 2D VEFMA has been computed for the case in which the field varies with a square wave. Resolution behaves similarly to that given by equation 26, but the constant of proportionality is lower:

$$R_Q \approx 0.08 \cdot k \qquad (30)$$

One could think that the square wave gives worse results than the sinusoidal wave, but if the generation of the square wave is simpler from the point of view of the power source and allows for the use of higher voltage, this disadvantage can be overcome and the total Resolution can be higher. The same applies to other wave shapes, including triangular wave shape.

As in Electronic Rotary VEFMA, the parameters used to control the selected mobility in the 2D VEFMA are the voltages and the frequency. In order to maximize the resolution, voltage should be as high as possible. In this circumstance, the frequency is the parameter which permits selecting the required mobility. The present invention is a narrow band mobility filter. But, by scanning over either the voltage or the frequency, it can be used as a scannable ion mobility spectrometer. The 2D VEFMA can be coupled with other systems such a MS. If coupled at the inlet of an MS, by turning off the time variable electric field, but maintaining the axial electric field, different ions having different mobilities entering through the inlet will reach the outlet slit driven by the axial electric field. Therefore, filtration by mobility can also be deactivated if desired.

The multistage 2D VEFMA: As above explained, the 2D VEFMA can handle much higher sample ion flows than the Rotary VEFMA having the resolution limited only by Brownian diffusion. However, the 2D VEFMA produces a strong pulsed signal of undesired ions having different mobility than the selected. Though said pulsed undesired signal can be post-processed, identified and separated from the steady signal, it can be a problem for certain applications.

Another means to drastically reduce the noise of the 2D configuration is using two equal stages of 2D VEFMA with an offset of their respective oscillating fields such that the pulses produced in the first stage are synchronized with the trajectories for which Y reaches its maximum value in the second stage. Note that, though the offset time at which the undesired ions reach the outlet slit of the first stage depends on the mobility of said undesired ions, the offset time for which ions entering the inlet slit of the second stage reach the highest Y also depends on said undesired mobility. Both offsets compensate each other and the pulsed signal is eliminated no mater what the undesired mobility is.

Figure 14:
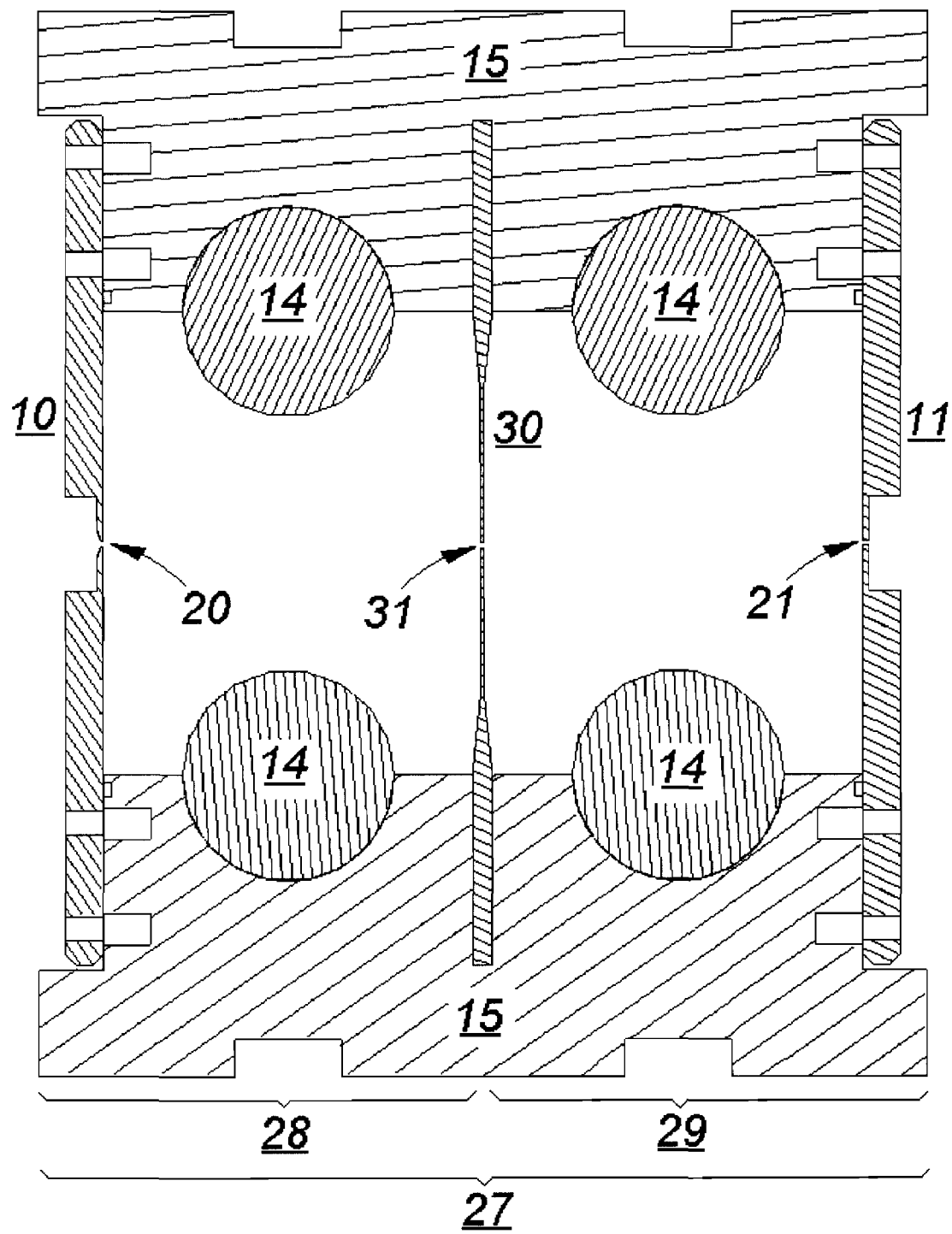
FIG. 14 illustrates a section view of the two stage 2D VEFMA.

Coupling two stages of 2D VEFMA is as easy as using the outlet electrode of the first stage as the inlet electrode of the second stage. FIG. 14 is a section view of a two stage 2D VEFMA (27) having a first stage (28) and a second stage (29). In this view, ions travel from left to right. Each stage works as a single 2D VEFMA similarly as the 2D VEFMA shown in FIGS. 9 and 10. The interface between the two stages is the intermediate electrode (30). The intermediate electrode acts as an outlet electrode for the first stage and as an inlet electrode for the second stage. An intermediate slit (31) is made in the intermediate electrode. Said intermediate slit acts as an outlet slit for the first stage and as an inlet slit for the second stage. Ions enter in the first stage (28) through the inlet slit (20) made in the inlet electrode (10). Ions are pushed towards the intermediate electrode (30) by the axial electric field which is produced by the voltage established between the inlet electrode (10) and the intermediate electrode (30). Ions reaching the intermediate slit (31) are pushed by the steady axial electric field through the intermediate slit and enter in the second stage (29). In the second stage (29), ions are pushed towards the outlet electrode (11) by the axial electric field which is produced by the voltage established between the intermediate (30) electrode and the outlet electrode (11). Each stage of the two stage 2D VEFMA comprises a set of deflectors (14), e.g., electrodes, grids and/or semiconducting surfaces, used to produce the oscillating electric field. Only the selected ions reach the outlet slit (21). Finally, insulators (15) are required to separate and to achieve a correct positioning of the different electrodes.

Figure 15:
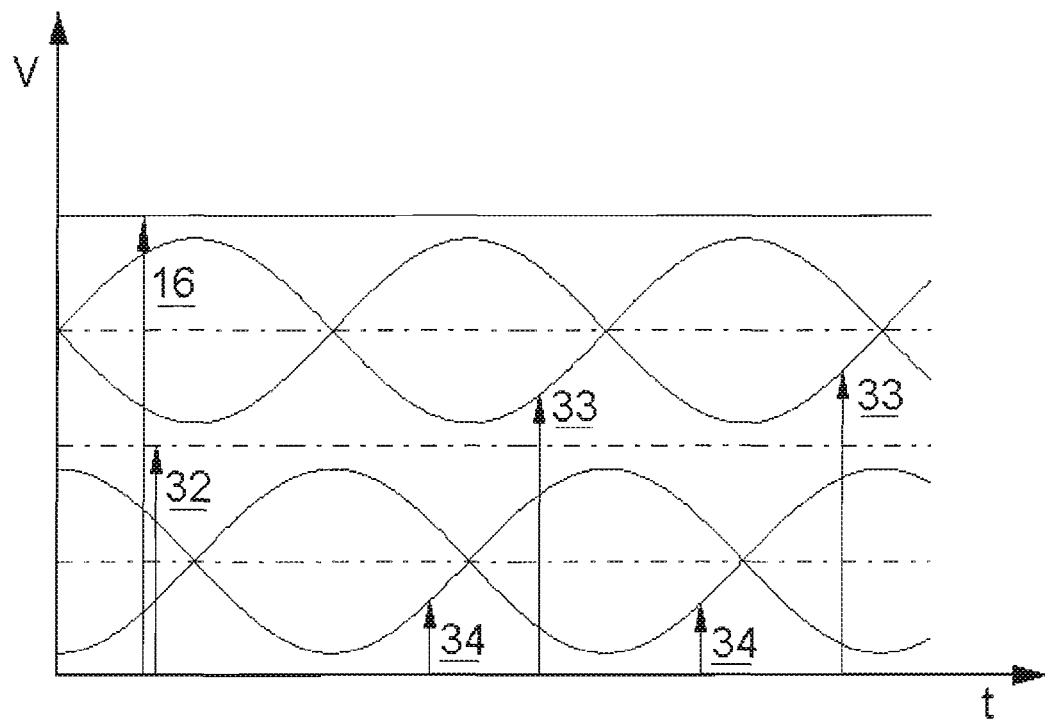
FIG. 15 illustrates schematically the voltage of the different electrodes of a two stage 2D VEFMA as a function of time.

FIG. 15 illustrates schematically the inlet electrode voltage (16), the intermediate electrode voltage (32), the two first stage deflector electrode voltages (33), and the second stage deflector electrode voltages (34), as a function of time. At each stage, each deflector electrode voltage comprises a wave of frequency $\Omega$ and a DC level. The waves of the first stage have an offset of approximately 90° with regard the waves of the second stage so that the oscillating electric fields of the first and second stages have an offset of approximately 90°.

The intermediate electrode voltage is half the inlet electrode voltage. The first stage deflector electrode DC voltage (33) is the mean of the inlet electrode voltage and the intermediate voltage. The second stage deflector electrode DC voltage (34) is half the intermediate electrode voltage. Each deflection voltage is therefore a sum of said wave and said DC voltage. In the preferred embodiment of the invention, the outlet electrode is the reference for the voltage upon which other voltages are defined.

Figure 16:
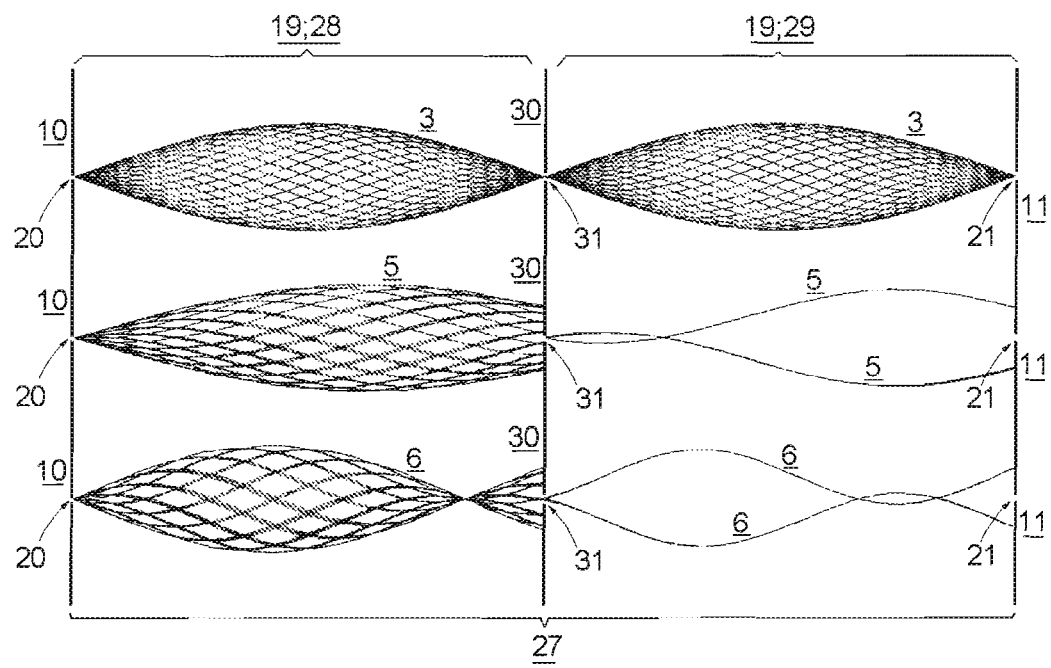
FIG. 16 illustrates schematically three different bundles of ion trajectories in an ideal two stage 2D VEFMA.

FIG. 16 represents three types of ion trajectory bundles in a two stage 2D VEFMA (27) composed by two ideal 2D VEFMA (19). For simplicity, only the inlet electrode (10), the intermediate electrode (30), and the outlet electrode (11) are depicted. Ions enter in the first stage (28) through the inlet slit (20) at different times. First top bundle shown is the selected bundle of trajectories (3), having the trajectories coalescing at the intermediate slit (31) and at the outlet slit (21), and corresponding to ions with the selected mobility. Second middle bundle shown is an overspeeding bundle of trajectories (5), corresponding to ions with higher mobility than the selected. And third bottom bundle shown is a lagging bundle of trajectories (6), corresponding to ions with lower mobility than the selected. FIG. 16 illustrates how the unselected ions reach periodically the intermediate slit (31). But, due to the offset between the first and the second stages, the trajectories of said undesired ions reaching the intermediate (31) slit are deflected in the second stage (29) far from the outlet slit (11). If the streak-tubes of ions are infinitesimally thin, unselected ions never reach the outlet slit and therefore pulsed undesired signal is avoided. However, in real configurations, the streak-tubes have a finite thickness and, though the majority of the undesired signal is avoided, pulsed signal is still produced for ions having mobilities closed to the selected.

Figure 17:
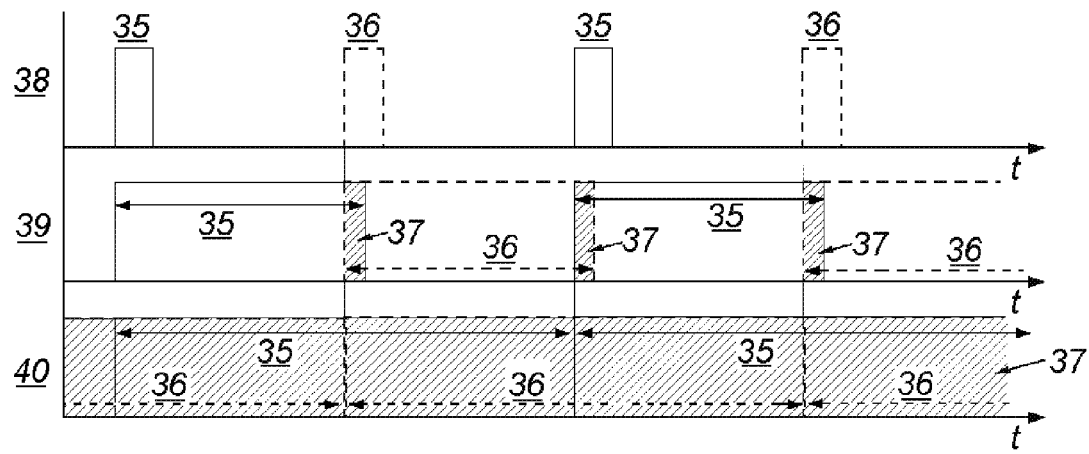
FIG. 17 illustrates schematically the pattern of pulsed windows and the output of selected mobility ions produced by a two stage 2D VEFMA.
Figure 18:
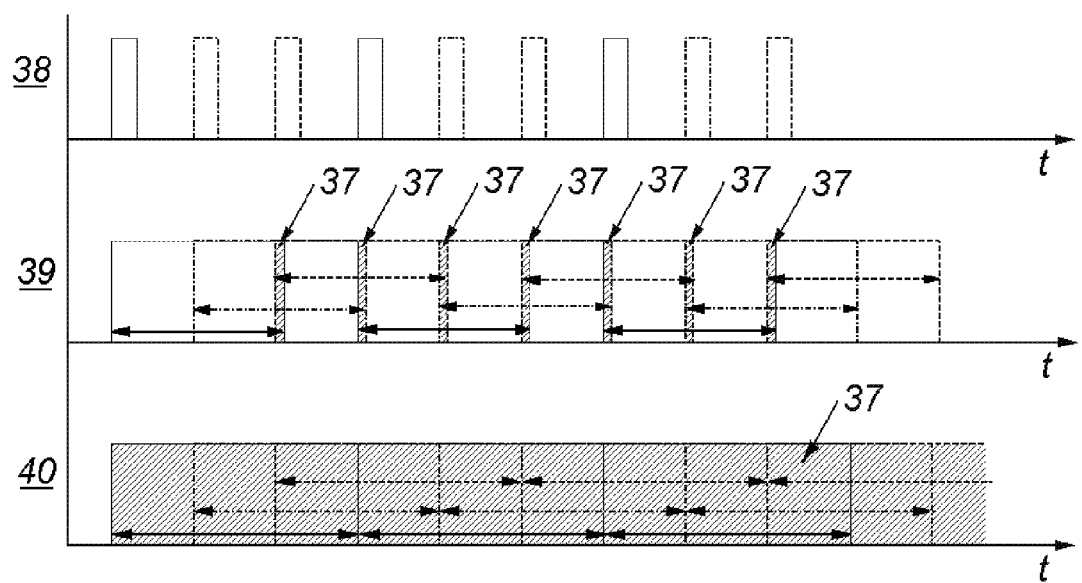
FIG. 18 illustrates schematically the pattern of pulsed windows and the output of selected mobility ions produced by a three stage 2D VEFMA.

FIG. 17 shows three different schemes of how the pulsed signals of ions at each stage are phased as a function of time. The continuous line (35) represents the time for which ions are reaching the intermediate slit. The dashed line (36) corresponds to the time for which, ions at the intermediate slit will reach the outlet slit. The PRI and PW characterizing said pulses are given by equations 24a and 24b. Only when both pulses are overlapped the ions can be transferred. In FIG. 16 this overlap is represented by a shadowed pulse (37). The first upper diagram represents the pattern produced by a mobility well separated from the selected mobility producing a non overlapping pulsed pattern (38). The second middle diagram represents the pattern produced by a mobility close enough to the selected producing a partially overlapped pattern (39) so that a pulsed noise is produced. And the third lower diagram represents the pattern produced by the selected mobility producing a totally overlapped pattern (40) so that a continuous output is produced. In this configuration, only those ions with mobility close to the selected mobility will be transferred. They will be transferred in pulses with a frequency of 4Ω and the selected mobility will be transferred in a continuous fashion. The discussion has been so far limited to the case where two stages of 2D VEFMA are coupled. However, more than two stages of 2D VEFMA could be used in a sequence to reduce the pulsed noise and increase resolution. Multistaging follows the same principles already discussed. This is shown in FIG. 18 in which, as an example, the pulsed patterns for the coupled stages are represented. In this case, the optimum offset between each stage is 60° rather than 90° (Note that, if n stages where used, the optimum offset would be 180°/n).

FIG. 18 shows three different schemes of how three phased pulsed windows of time during which ions would be transferred in each of the stages of the three stage 2D VEFMA. The ions are transferred only when the three sets of windows are overlapped. This is shown by the shadowed overlapping pulses (37). As in FIG. 17, the first upper diagram represents the pattern produced by a mobility well separated from the selected mobility producing a non overlapping pulsed pattern (38). The second middle diagram represents the pattern produced by a mobility close enough to that selected producing a partially overlapped pattern (39) so that a pulsed noise is produced. And the third lower diagram represents the pattern produced by the selected mobility producing a totally overlapped pattern (40), resulting in a continuous output. In this configuration, undesired ions having mobilities close to that selected will be transferred in pulses with a frequency of 6Ω and the selected mobility will be transferred in a continuous fashion.

The averaged gain $s_n$ produced by a multistage 2D VEFMA can be easily related to the averaged gain produced by each single stage and is given by the following equation:

$$s_n = \begin{cases} s_1 \in \left(0, 1 - \frac{1}{n}\right) \Rightarrow s_n = 0 \\ s_1 \in \left(1 - \frac{1}{n}, 1\right) \Rightarrow s_n = 1 + n \cdot (s_1 - 1) \end{cases} \quad (31)$$

where $s_n$ is the averaged gain of the multistage 2D VEFMA, $s_1$ is the averaged gain produced by each single stage, and n is the total number of stages. Multistage schemes reduce the pulsed noise and also increase the resolution. The resolution of a two stage 2D scheme has been computed and it has been found to be 30% higher than that computed for each single stage.

Figure 19:
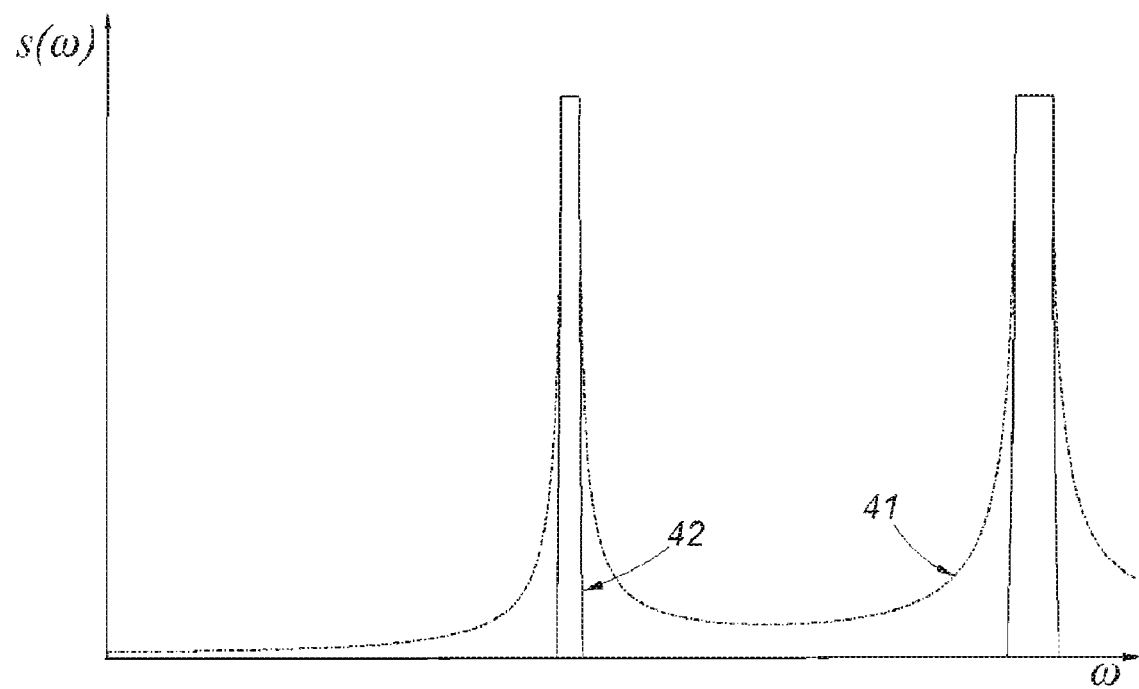
FIG. 19 illustrates the gain of a 2D VEFMA as a function of the dimensionless parameter ω for a two stage 2D VEFMA and a single stage 2D VEFMA.

FIG. 19 represents the functions $s_1(\omega)$ (41) and $s_2(\omega)$ (42) according to equations 25 and 31. As above mentioned, the functions $s_1(\omega)$ and $s_2(\omega)$ can be interpreted as the gain of a single 2D VEFMA and a two stage 2D VEFMA for a given ion as a function of the dimensionless frequency of the oscillating electric fields. In FIG. 18, the function $s_1(\omega)$ (41) is represented by a dashed line wile the function $s_2(\omega)$ (42) is represented by the continuous line. Note that, though the resolution has not been increased much, the pulsed noise has been drastically reduced.

Tandem VEFMA-VEFMA can also be used to measure the non linearity in the mobility of ions and to separate ions having the same mobility in the linear region, but different values in the nonlinear regime. The concept is exactly the same as the already proposed tandem DMA-DMA by J. Fernández de la Mora and colleagues (See U.S. patent application Ser. No. 12/070,937) having one VEFMA working at higher electric velocity than the other VEFMA. However, the VEFMA systems can achieve higher resolutions and can be coupled more easily. Indeed, the outlet orifice of the first stage can be at the same time the inlet orifice of the second stage. By this way, transmission loses can be virtually reduced to zero. For this configuration, either Rotary VEFMA or 2D VEFMA or multistage 2D VEFMA can be used. And no deflector electrode voltage synchronization is required.

In the general case, the VEFMA inlet and the VEFMA outlet are orifices or slits. As above mentioned, it is very important to have the inlet and the outlet correctly aligned. Ions can be driven through said orifices or slits either by the electric field or by the fluid velocity. The fluid field can not be made perfectly symmetrical in the region used to filter ions because, when entering in the VEFMA, detached jets are produced while, when exiting the VEFMA, an attached sinklike configuration is produced. The electric field is not subjected to detachment effects and symmetrical configurations can be easily achieved if ions are driven through the inlet and outlet by said electric fields. Therefore, it is advisable to introduce and extract the ions in a VEFMA by means of electric fields that permit more symmetrical configurations; nonetheless, in some specific applications it can be more advisable to drive the ions through the VEFMA inlet and outlet by means of fluid velocities. A sheath gas can also exit through the VEFMA inlet to assure that the VEFMA is kept clean. To do so, clean gas has to be introduced in the VEFMA through an auxiliary gas inlet. In order to prevent the formation of turbulent jets inside the VEFMA, said auxiliary gas inlet has to be large to produce very low fluid velocities and low Reynolds for a given flow rate. Laminarization meshes can be used in said auxiliary gas inlet to prevent turbulence.

Using a controlled gas is important to measure the mobility under a controlled situation. As the gas is continuously introduced in the VEFMA, different gasses can be selected according to their properties. For instance, $N_2$ is cheap to produce, while $CO_2$ or $SF_6$ can be used to increase the maximum electric field (the electric field is limited by the onset of electric discharges which depends on the gas utilized) inside the VEFMA. Note that increasing the electric field permits reducing the size of the VEFMA while maintaining its resolution and this can be useful to make miniaturized lightweight VEFMA. Miniaturized VEFMA should work at higher frequencies. An electrostatic shielding isolating the electric fields within the VEFMA from the electric fields outside the VEFMA can be useful to prevent external perturbations of the electric field inside the VEFMA and to prevent possibly harmful electromagnetic emissions produced by the VEFMA. Said shielding can be easily made by a conductor box enclosing the VEFMA.

Heating the VEFMA is as easy as heating its parts. Heated VEFMA can be used to prevent depositions that would contaminate it. Cooled or Cryogenic VEFMA can also be used to drastically increase its resolution. Note that Brownian diffusion grows with the temperature. VEFMA can easily be heated or cooled because it does not have mechanical parts. In contrast, it is difficult to heat or cool a DMA because the required leak tight pump producing the fast required velocity field usually has a narrow range of temperatures, and because temperature gradients in the DMA channel can induce natural convection velocities which can induce turbulence, and therefore spoil the resolution.

As above mentioned, VEFMA selects a set of different ions according to the criterion $\omega = n \cdot \pi$; (n=1, 2, 3 . . . ) The resulting multiplicity of selected ions can be avoided by means of a high-pass mobility filter. Said high-pass mobility filter is placed in series with the VEFMA preferably before the ions can reach the entrance to the VEFMA. Many configurations produce the required rough ion mobility filtration. Said high-pass mobility filter can be coupled upwards or downwards the VEFMA. If the VEFMA is coupled in a sequence of analyzers, the rough filter can also be placed in any stage of the sequence. Another analyzer can also substitute the high-pass mobility filter. The VEFMA can also work without the high-pass mobility filter if the separation of the whole family of ions given by equation 12b is suitable for the specific application. There are many possible configurations regarding the high-pass mobility filter and they are all part of the present invention. For instance, FIG. 20 illustrates a high-pass mobility filter (43).

Figure 20:
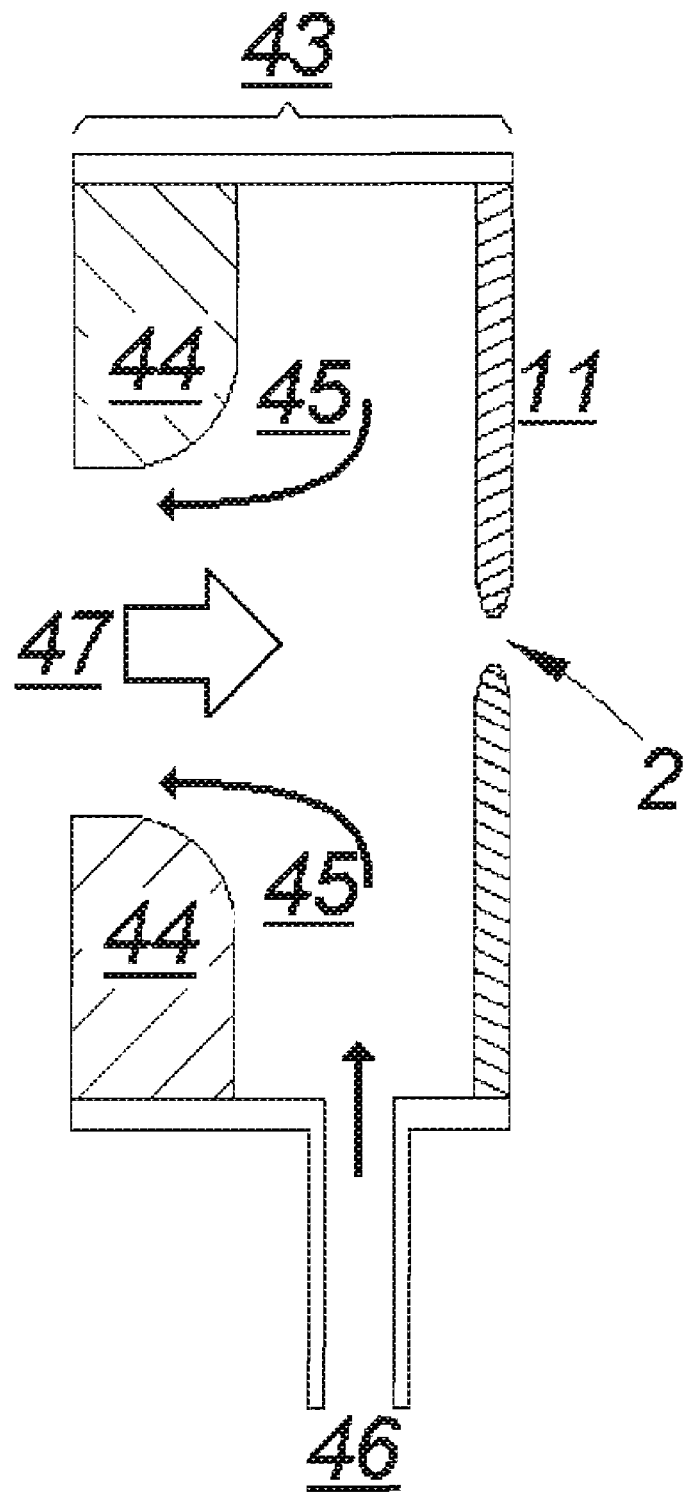
FIG. 20 illustrates schematically a High-pass mobility filter tailored to the VEFMA inlet.

In FIG. 20, a nozzle (44) accelerates the low mobility sweeping gas (45) to push the low mobility ions backwards. The space between the accelerating nozzle and the inlet electrode (11) is termed the clean region. Low mobility sweeping gas is introduced in the clean region to feed the nozzle through the low mobility sweeping gas inlet (46). An electric field named the high pass electric field (47) has to be induced within the nozzle (44) and between the nozzle and the inlet electrode (11) to push the high mobility ions forward into the VEFMA inlet (2). The ratio between the low mobility sweeping gas velocity and the high pass electric field has to be tuned with the selected mobility in order to assure separation between ions corresponding to different filtered mobilities given by n=1 and n=2 in the VEFMA. Since the required resolution has to be only higher than two, neither high electric fields nor fluid speeds are required in the high-pass mobility filter. The low mobility sweeping gas and the gas inside the VEFMA can have different composition. The high-pass mobility filter (43) used at the VEFMA inlet ensures that the VEFMA is kept clean and no sheath gas emerging from the VEFMA inlet is required unless different gases are required inside the VEFMA and in the low mobility sweeping gas. The high mobility pass filter required in a 2D VEFMA stands on the same principles as the high mobility pass filter for the rotary VEFMA. Hence, one only needs to replace the circular orifices aligned with the orifice inlet by slits following the inlet slit.

VEFMA-API-MS: When coupling a VEFMA with an API MS interface, it is advantageous to move the ions towards the sonic orifice of the MS with the flow. If ions are extracted from the VEFMA by means of fluid velocity, the outlet of the VEFMA can be simultaneously the inlet of the MS. For the Rotary VEFMA, a straight axi-symmetrical orifice can drive effectively the ions from the VEFMA to the vacuum side of the MS. Special attention is required to accommodate the transition from the outlet slit geometry of 2D VEFMA to the circular orifice inlet typical of the MS. This transition can be achieved by means of using a shaped orifice of transition through a plate comprising a slit in the side facing the 2D VEFMA and an orifice in the other side facing the skimmer of the API-MS. This orifice will have to substitute the original sampling orifice of the API-MS to which coupling is required. The mission of this orifice is to produce a fluid velocity field to couple the two different geometries. This solution has already been implemented by J. Rus and J. Fernandez de la Mora for coupling a planar (2D) DMA to several MS.

If the ions are extracted by the VEFMA by means of electric velocity, an intermediate chamber between the VEFMA outlet and the MS inlet is required. In this chamber, the gas sampled by the MS is introduced through an auxiliary gas inlet. Ions pushed by the electric fields of the VEFMA outlet also enter in this chamber and, after mixing with the auxiliary gas; both the gas and the ions are sampled by the MS through the sonic inlet orifice of the MS. Other advantage of this intermediate chamber is that it permits working with different gases in the VEFMA and in the MS.

Ions to be analyzed by the VEFMA have to be produced at relatively high pressure. An Electrospray ion source can be used to produce ions at atmospheric pressure, though various other sources of ions can be used as well. Well known examples of unipolar and bipolar ionization sources include radioactive materials, corona discharges, and other sources of ionizing radiation (UV light, X rays, etc.). Other ionization sources that can be used include Secondary Electrospray Ionization Sources and proton transfer reaction for vapor ionization; see U.S. patent application Ser. No. 11/732,770. More complex systems to ionize vapors can also be used as a source of ions, see U.S. Provisional Patent Application 61/204,996. The scheme proposed in U.S. Provisional Patent Application 61/204,996 is especially advantageous to avoid dilution of the vapors to be ionized by the flow of a high mobility pass filter. The VEFMA system can also be coupled with an ion pre-concentration device such as a quadrupole (See U.S. provisional patent application US60/857,231). Also the outlet of a complementary analyzer can be used as a source of pre-filtered ions.

VEFMA Compared with Other Mobility Filters.

Ion Mobility Spectrometers (IMS) do not require high velocity flows and can also be used as narrow band mobility filters when both the inlet and the outlet gates are opened and closed with an offset time so that only a narrow band of the entire spectrum generated in the drift tube is transferred through the outlet gate. This procedure is a synchronization of the time of residence inside the analyzer and the offset time of aperture of the gates. In a VEFMA, the gates are always opened and the synchronization occurs between the time of residence of the selected ions and the characteristic time of the variable electric field. From the perspective of the user, there are two main differences between a VEFMA and an IMS: (i) the transmission of ions in the VEFMA is continuous while the transmission of ions in an IMS is pulsed. (ii) And the transmission of a VEFMA system reaches nearly 100%. This value is similar to that obtained for DMAs that also have their inlet and outlet continuously opened. This value is much higher than that obtained by IMS because those systems pass ions only over a small fraction of the time, typically 1%.

Clemmer et al. explain that they accomplish filtration by changing the drift field at a frequency that is resonant with the ion's drift time through each region. Note that the selected ions are only affected by the favorable part of the cycle of the varying electric field that pushes the ions upwards in each stage of the cyclotron, while other ions are stopped by the unfavorable electric field. Selected ions are thus always subjected to the favorable and steady part of the electric field cycle as if they where traveling through a multistage drift tube with steady electric fields and far more than four drift tubes, ion funnels and gates. In contrast, every selected ion treated in a VEFMA system is subjected to at least one full cycle of the variable electric fields Ions travel along the apparatus developed by Clemmer et al. as if they were in a multistage scheme composed of several drift tubes, ion funnels and gates. Consequently, ions are forming packets and the output signal is pulsed, as it is in any other IMS system used as a filter by means of gate synchronization, and therefore the scheme presented by Clemmer is also subjected to a small duty cycle.

In a drift tube based system, no matter what their mobility is, all ions travel approximately through the same trajectory near the axis of the drift tube. The difference in trajectories between selected and non selected ions can be only found in the gates where lagging and overspeeding ions are chopped from the pack of ions spread in the drift tube. The outlet signal of ions emerging from drift tube based systems has to be pulsed because separation is produced in time. As a consequence of the pulsed output of ions, the duty cycle is small. In contrast, in a VEFMA, the trajectories of the different ions differ from each other because the whole electric field is varied in time. As the different ions are geometrically separated, the outlet of filtered ions can be smooth and continuous, and the duty cycle can be up to 100%.

DMAs are natural competitors of the VEFMA since both types of apparatus measure directly the mobility of ions and particles and produce a continuous output of selected ions. The main advantages of VEFMAs over DMAs are: (i) No high fluid velocity field is required and there are no limitations and problems caused by the onset of turbulence (limited Reynolds), mechanical noise, and the sonic limit in the speed of the flow field. Thus, the resolution achievable by a VEFMA system is higher. (ii) The inlet and the outlet of the VEFMA are very accessible as they are placed in planar plates. Thus, the VEFMA can easily be coupled to a MS system or any other ion measurement system. (iii) The inlet and outlet are perfectly aligned in the VEFMA. Thus, the final user will not be required to change any special settings if the user does not want to filter a specific mobility. Turning off the variable electric field will be enough to stop mobility filtration since the steady streamlines will guide ions of all mobilities from the VEFMA inlet to the VEFMA outlet. (iv) As VEFMA does not require a pump, limitations associated to said pump are avoided, for example the range of temperatures for which VEFMA can operate is much wider.

The VEFMA uses variable electric fields like FAIMS, but there are two main differences between both systems. (i) VEFMA measures mobility while FAIMS measures non linear behavior of the mobility. (ii) During their residence in the apparatus, the ions with selected mobility suffer at least one full cycle of the variable field of the VEFMA and are quickly pushed away from the analyzer by the axial electric field. While ions crossing a FAIMS suffer many cycles of the asymmetric field and are pushed just by a slight velocity produced by the flow carrying the ions through the FAIMS chamber. This implies that the time of residence, and thus diffusion, is much shorter in a VEFMA than in a FAIMS; leading to higher resolution and higher transmission in the VEFMA.

FAIMS and VEFMA can be used similarly as filters, coupled with other detectors like MS, or as simple ion detectors comprising a Faraday cup electrometer. However, both different systems can also be coupled to each other. Hence, it is possible to extract information about the mobility through the VEFMA and about the non linear mobility behavior through the FAIMS. Coupled FAIMS and VEFMA can be used as filters, they can also be coupled to an MS, and they can also be used as a detector comprising a Faraday cup electrometer. VEFMA by itself can measure mobilities both in the linear and the nonlinear regions.

What is claimed:

1. An apparatus for providing a continuous beam of selected ions filtered according to their electrical mobility, said apparatus comprising:
   an inlet;
   an outlet;
   a plurality of axial electrodes configured to produce an axial electric field in the direction of a central axis defined from the inlet towards the outlet; and,
   a plurality of deflector electrodes, symmetrically arranged around the central axis, powered with a combination of steady and periodically varying voltages configured to define a periodic deflector electric field, such that,
   trajectories of ions are caused to move away from the central axis during a half cycle of the periodic deflector electric field, and trajectories of the ions are moved towards the central axis during the remainder of the cycle of the periodic deflector electric field,
   wherein, after a cycle of the periodic deflector electric field, ion trajectories coalesce continuously to the central axis with only ion trajectories of the selected ions coalescing continuously to the outlet.

2. An apparatus as in claim 1, wherein said axial electrodes and/or said deflector electrodes are selected from conducting surfaces, grids, and/or semiconducting surfaces, and wherein said deflector electrodes are configured symmetrically with respect to a plane equidistant from said inlet and said outlet.

3. An apparatus as in claim 1, wherein,
said inlet and outlet are approximately round and are coincident with the central axis, and
the periodic deflector electric field rotates about said central axis and is generated by several among said deflectors symmetrically spaced apart, each equidistant from said central longitudinal axis, and each powered by periodic voltages with symmetrically shifted phases.

4. An apparatus as in claim 1, where said inlet and said outlet are both linear slits with their length oriented along a given lateral direction perpendicularly to the central axis, the periodic deflector electric field oscillates perpendicularly to the lateral direction and the central axis, and is generated by several among the deflector electrodes symmetrically spaced with respect to a plane containing the central axis, the lateral direction, said inlet, and said outlet.

5. An apparatus as in claim 4, further comprising means to detect ions passing through said outlet, and including a signal analyzer to detect and separate pulsed phase shifted signals from a continuous signal obtained by said means to detect ions.

6. An apparatus as in claim 1, further comprising means to detect ions passing through said outlet.

7. An apparatus as in claim 1, further comprising a chamber between said inlet and said outlet configured to accommodate a gas at rest through which electrical mobility is to be considered.

8. An apparatus constituted by N stages, each stage including one apparatus as in claim 4, where the outlet of a stage is connected in series to the inlet of the succeeding stage, all stages being driven at the same electric field strength and frequency to filter the same ions, with the periodic electric fields of succeeding stages being phase shifted with respect to each other by approximately 180°/N such that pulsed output of a stage is eliminated in subsequent stages with ion trajectories of non-selected ions not reaching the outlet of a last of the stages of the apparatus.

9. An apparatus as in claim 1 including a source of clean gas flowing into said apparatus, part of said flow of gas leaving the apparatus as one or both of the following:
  i) counterflow gas through said inlet;
  ii) sample gas through said outlet.

10. An apparatus as in claim 1 further including an external ion source, and electric fields to guide ions produced by said external ion source through said inlet for mobility separation.

11. An assembly comprising:
an apparatus formed in accordance with claim 1; and
a high mobility pass filter having a resolution higher than 2.

12. An assembly comprising:
an apparatus formed in accordance with claim 1; and
means to analyze ions passing through said outlet orifice of said outlet electrode.

13. An assembly as in claim 12, wherein said means to analyze ions is selected from the group consisting of a mass spectrometer, a FAIMS, and a DMA.

14. An assembly as in claim 12, wherein said means to analyze ions is a second apparatus formed in accordance with claim 1.

15. An assembly as in claim 14, wherein the strength of said electric field of said second apparatus is different from the strength of said electric field of said first-mentioned apparatus.

16. An assembly as in claim 14, wherein the composition of the gas in the second apparatus is different from that of the first apparatus.

17. An assembly as in claim 12, further comprising a chamber between said outlet and said means to analyze ions, and an auxiliary inlet for introducing clean gas into said chamber.

18. A method to separate selected ions according to their electrical mobility in a gas at rest, the method comprising:
introducing ions continuously through an inlet in a chamber defined between said inlet and an outlet, a central axis being defined from said inlet towards said outlet, with said chamber containing a gas at rest through which electrical mobility is to be measured;
urging ions through the gas along a direction towards said outlet by means of a steady axial electric field; and,
generating a periodic deflector electric field by a plurality of deflector electrodes, symmetrically arranged about said central axis, said deflector electrodes powered with a combination of steady and periodically varying voltages configured to define said periodic deflector electric field, such that,
ions are driven away from said central axis during a half cycle of said periodic deflector electric field, and ions are driven back towards said central axis during the remainder of the cycle of said periodic deflector electric field,
wherein, after a cycle of said periodic deflector electric field, ion trajectories coalesce continuously to said central axis with only trajectories of the selected ions coalescing continuously to said outlet.

19. A method as in claim 18, wherein,
said inlet and outlet are approximately round and are coincident with said central axis, and
said periodic deflector electric field is rotating about said central axis, and is generated by several among said deflector electrodes symmetrically spaced apart, each equidistant from said central axis, and each powered by periodic voltages with symmetrically shifted phases.

20. A method as in claim 18, where:
said inlet and said outlet are both linear slits with their length oriented along a given lateral direction perpendicularly to said central axis,
said periodic deflector electric field is oscillating perpendicularly to said lateral direction and said central axis, and is generated by several among said deflector electrodes symmetrically spaced with respect to a plane containing said central axis, said lateral direction and said inlet and outlet slits.

* * * * *